United States Patent
Gilliet et al.

(10) Patent No.: US 10,751,416 B2
(45) Date of Patent: Aug. 25, 2020

(54) IL-26 INHIBITORS

(71) Applicants: CENTRE HOSPITALIER UNIVERSITAIRE VAUDOIS (CHUV), Lausanne (CH); BOARD OF REGENTS, THE UNIVERSITY OF TEXAS SYSTEM, Austin, TX (US)

(72) Inventors: Michel Gilliet, Lausanne (CH); Jeremy Di Domizio, Lausanne (CH); Stephan Meller, Cologne (DE)

(73) Assignees: CENTRE HOSPITALIER UNIVERSITAIRE VAUDOIS (CHUV), Lausanne (CH); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 25 days.

(21) Appl. No.: 15/744,254

(22) PCT Filed: Jul. 13, 2016

(86) PCT No.: PCT/EP2016/066688
§ 371 (c)(1),
(2) Date: Jan. 12, 2018

(87) PCT Pub. No.: WO2017/009392
PCT Pub. Date: Jan. 19, 2017

(65) Prior Publication Data
US 2018/0207271 A1    Jul. 26, 2018

(30) Foreign Application Priority Data
Jul. 13, 2015   (EP) .................................... 15176537

(51) Int. Cl.
| | | |
|---|---|---|
| *A61K 39/395* | (2006.01) | |
| *A61K 38/13* | (2006.01) | |
| *C07K 16/24* | (2006.01) | |
| *A61P 17/06* | (2006.01) | |
| *A61K 39/00* | (2006.01) | |
| *A61K 31/194* | (2006.01) | |
| *A61K 31/505* | (2006.01) | |

(52) U.S. Cl.
CPC ........ *A61K 39/39566* (2013.01); *A61K 38/13* (2013.01); *A61P 17/06* (2018.01); *C07K 16/244* (2013.01); *A61K 31/194* (2013.01); *A61K 31/505* (2013.01); *A61K 2039/505* (2013.01); *A61K 2300/00* (2013.01); *C07K 2317/24* (2013.01); *C07K 2317/76* (2013.01); *Y02A 50/414* (2018.01)

(58) Field of Classification Search
None
See application file for complete search history.

(56) References Cited

U.S. PATENT DOCUMENTS

2003/0073199 A1 * 4/2003 de Waal Malefyt ........................ C07K 14/5428
435/69.52

OTHER PUBLICATIONS

Stephen-Victor E, Fickenscher H, Bayry J (2016) IL-26: An Emerging Proinflammatory Member of the IL-10 Cytokine Family with Multifaceted Actions in Antiviral, Antimicrobial, and Autoimmune Responses. PLoS Pathog 12(6): e1005624. https://doi.org/10.1371/journal.ppat.1005624 (Year: 2016).*
Sara Tengvall, Karlhans Fru Che, Andres Linden (2016) Interleukin-26: An Emerging Player in Host Defense and Inflammation. J. Innate Immun: 8, p. 15-22. (Year: 2016).*
Lloyd et al. (2009) Protein Engineering, Design & Selection 22:159-168, 2009 (Year: 2009).*
Dec. 9, 2016 Written Opinion of the International Searching Authority issued in Patent Application No. PCT/EP2016/066688.
Dec. 9, 2016 International Search Report issued in Patent Application No. PCT/EP2016/066688.
Labome, "Human IL-26/AK155 MAb (Clone 197505), R and D Systems MAB1375 Product Information", https://www.labome.com/producr/R-and-D-Systems/MAB1375.html, (2009).
Braum, Oliver et al., "The Cationic Cytokine IL-26 Differentially Modulates Virus Infection in Culture.", PLOS ONE, vol. 8, No. 7, pp. 1-17, (2013).
Meller, Stephan et al., "TH17 cells promote microbial killing and innate immune sensing of DNA via interleukin 26.", Nature Immunology, vol. 16, No. 9, pp. 970-979, (2015).

* cited by examiner

*Primary Examiner* — Daniel E Kolker
*Assistant Examiner* — Jegatheesan Seharaseyon
(74) *Attorney, Agent, or Firm* — Oliff PLC

(57) ABSTRACT

The present invention relates to methods and compositions for the therapeutic and diagnostic use in the treatment of diseases and disorders which are caused by or associated with interleukin 26 (IL-26), including inflammatory diseases, such as psoriasis and/or bacterial infections.

13 Claims, 21 Drawing Sheets
Specification includes a Sequence Listing.

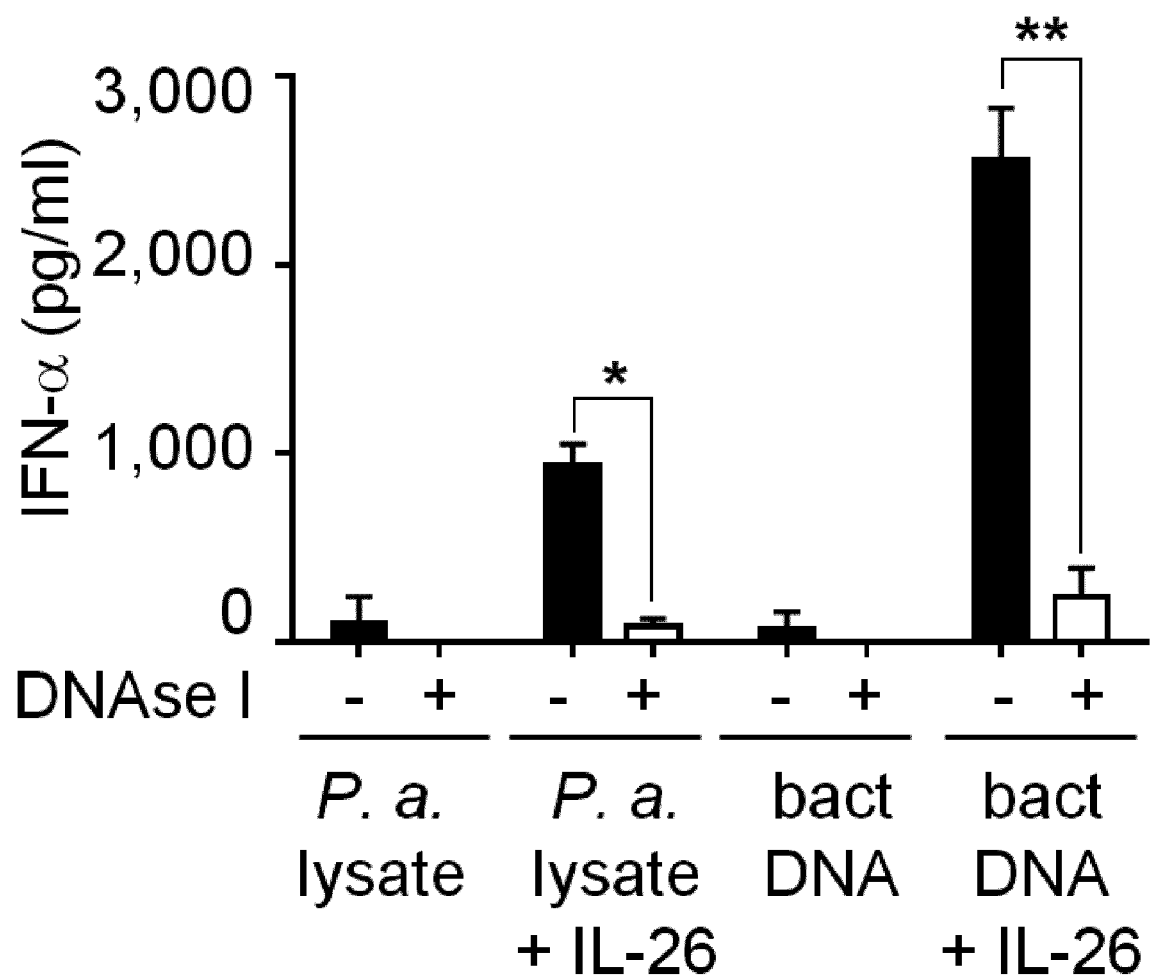

IL-26 INHIBITORS

TECHNICAL FIELD

The present invention relates to methods and compositions for the therapeutic and diagnostic use in the treatment of diseases and disorders which are caused by or associated with interleukin 26 (IL-26), including inflammatory diseases, such as psoriasis and/or bacterial infections.

BACKGROUND OF THE INVENTION

Interleukin 26 (IL-26) also known as AK155 is a 19-kDa α-helical protein that belongs to the IL-20 cytokine family. IL-26 was first identified in herpesvirus saimiri-transformed T cells, and subsequently found to be conserved in most vertebrate species but absent in mice. Like other TH17 cytokines, IL-26 is highly expressed in psoriatic skin lesions (Wilson N J et al, Nat Immunol 2007, 8(9): 950-957), colonic lesions from patients with inflammatory bowel disease (Dambacher J, et al, Gut 2009, 58(9): 1207-1217), and synovia of rheumatoid arthritis patients (Corvaisier M, et al, PLoS Biol 2012, 10(9): e100139) and is strongly associated with inflammatory activity. A risk locus containing the IL-26 gene and single nucleotide polymorphisms (SNPs) within the IL26 gene region were associated with multiple sclerosis (Goris A, et al, Genes Immun 2001, 2(5): 284-286), rheumatoid arthritis (Vandenbroeck K, et al, Arthritis Rheum 2003, 48(10): 2773-2778) and inflammatory bowel disease (Silverberg M S, et al, Nat Genet 2009, 41(2): 216-220) suggesting a particularly important role of IL-26 in TH17-mediated inflammatory disease.

IL-26 was shown to signal through the IL-10R2-IL-20R1 heterodimeric receptor expressed exclusively by epithelial cells (Hor S, et al, J Biol Chem 2004, 279(32): 33343-33351 and, Sheikh F, et al, J Immunol 2004, 172(4): 2006-2010). Via its receptor, IL-26 was found to inhibit the proliferation of intestinal epithelial cells and, in parallel, to induce expression of immunosuppressive IL-10 but also the pro-inflammatory cytokines TNF and IL-8.

Furthermore, IL-26 and other interleukins such as IL-17A, IL-17F, IL-21, IL-22 are produced by Human T helper 17 (TH17) cells, a subset of T cell that drive inflammatory responses by producing and IL-26 (Wilson N J, et al, Nat Immunol 2007, 8(9): 950-957). Defective TH17 responses in patients deficient in the transcription factor STAT3 have been associated with increased susceptibility to *Staphylococcus aureus* and *S. pyogenes* infections (Ma C S, et al, J Exp Med 2008, 205(7): 1551-1557) indicating that this T cell subset plays a major role in the defense against extracellular bacterial infections particularly in the skin and mucosal surfaces. On the other hand, excessive TH17 cell responses drive chronic inflammation and the development of autoimmunity in predisposed individuals. TH17-associated cytokines were indeed associated with disease activity and found to be increased in the skin of psoriasis, in the intestine of Crohn's disease, in the brain of multiple sclerosis and the synovium of rheumatoid arthritis and ankylosing spondylitis patients (Gaffen S L et al, Nature reviews Immunology 2014, 14(9): 585-600).

US 2003/0073199 A1 (DNAX RESEARCH, INC.) discloses purified genes encoding a cytokine from a mammal, reagents related thereto including purified proteins, specific antibodies, and nucleic acids encoding this molecule are provided. Methods of using said reagents and diagnostic kits are also provided. The document further provides a method of treating a patient having an immune or inflammatory response by administering an effective dose of an antibody or binding partner for AK155.

WO 03/002717 (Schering Corporation.) and US 2003/0108958 (DNAX RESEARCH, INC.) relate to cells that express a recombinant AK155 receptor, methods for screening for agent that modulates the effects of an AK155 on an AK155 receptor, and for methods of treating disease using agents that modulate the interactions between an AK155 and an AK155 receptor. In these technologies the new function of IL-26 (AK155) is receptor-dependent and the developed antibodies are directed to the IL-26 receptor binding site.

Therefore, modulating (activating or blocking) the effects of IL-26 might represent an attractive modality for the treatment of inflammatory related diseases and/or bacterial infections. Further, in the management of inflammatory diseases and/or bacterial infections, there is a need for a modulator which is effective without eliciting secondary effects.

SUMMARY OF THE INVENTION

Psoriasis is a common chronic-relapsing inflammatory skin disease initiated by activation of plasmacytoid dendritic cells (pDC) and mediated by Th17 cells producing IL-17A/F, IL-22 and IL-26. While the functions of IL-17 and IL-22 are well characterized, the role of IL-26 in the inflammatory process is less clear. Here Applicants have surprisingly found that TH17-derived IL-26 has a cationic amphipathic structure, which allows direct killing of extracellular bacteria via membrane pore formation. Furthermore, TH17-derived IL-26 formed complexes with bacterial- and self-DNA released by dying bacteria or host cells, respectively. The resulting IL-26-DNA complexes triggered potent type I IFN production by pDC via Toll-like receptor 9 activation. In psoriasis IL-26 was highly expressed in lesional skin, reaching levels relevant for pDC activation. Moreover, repetitive skin injection of IL-26 induced type I IFN production by pDC and the development of a psoriatic phenotype in mice. These findings identify an antimicrobial and pro-inflammatory function of TH17-derived IL-26 and demonstrate a key role in the pathogenesis of psoriasis and potentially other chronic inflammatory diseases.

It is an object of the present invention to provide an isolated monoclonal antibody or biological active fragment thereof that recognizes and binds IL-26, comprising: a heavy chain variable region that comprises CDR1, CDR2, CDR3 sequences and a light chain variable region that comprises CDR1, CDR2, CDR3 sequences wherein:

(a) the heavy chain variable region CDR1 sequence comprises the amino acid sequence of SEQ ID NOs: 5 or conservative modifications thereof;

(b) the heavy chain variable region CDR2 sequence comprises the amino acid sequence of SEQ ID NOs: 6 or conservative modifications thereof;

(c) the heavy chain variable region CDR3 sequence comprises the amino acid sequence of SEQ ID NOs: 7 or conservative modifications thereof;

(d) the light chain variable region CDR1 sequence comprises the amino acid sequence of SEQ ID Nos 8 or conservative modifications thereof;

(e) the light chain variable region CDR2 sequence comprises the amino acid sequence of SEQ ID Nos 9 or conservative modifications thereof;

(f) the light chain variable region CDR3 sequence comprises the amino acid sequence of SEQ ID Nos 10 or conservative modifications thereof.

Preferably the isolated monoclonal antibody or a biological active fragment thereof capable of recognizing and binding IL-26 comprises:

i) a Heavy Chain Variable Region (HCVR) comprising the amino acid sequence of SEQ ID NO:3, and ii) a Light Chain Variable Region (LCVR) comprising the amino acid sequence of SEQ ID NO:4.

Further the invention also provides for a nucleic acid molecule comprising a nucleotide sequence encoding the monoclonal antibody or biological active fragment thereof.

Also provided is an expression vector comprising the nucleotide sequence of the invention and a cell comprising the expression vector of the invention.

It is another object of the invention to provide a pharmaceutical composition comprising the monoclonal antibody or the biological active fragment thereof and optionally further comprising a pharmaceutically acceptable carrier.

In another embodiment, the invention relates to a hybridoma deposited under an ATCC accession number of PTA-122358 filed on Jul. 10, 2015.

It is another object of the invention to provide a monoclonal antibody that recognizes and binds IL-26 and having the same epitope specificity as the monoclonal antibody produced by hybridoma cell line 142-84-B1, ATCC accession number PTA-122358.

In a further embodiment of the invention, it is provided an isolated monoclonal antibody that recognizes and binds IL-26, and wherein said isolated monoclonal antibody is produced by hybridoma cell line 142-84-B1, ATCC accession number PTA-122358.

Also provided is a pharmaceutical composition comprising the isolated monoclonal antibody or the biological active fragment thereof according to the invention, and optionally further comprising a pharmaceutically acceptable carrier.

The present invention also provides for an inhibitor of the expression or activity of IL-26, for use in the treatment or alleviation of the effects of inflammatory diseases, wherein said inhibitor of the expression or activity of IL-26 is selected among the group comprising, the IL-26 monoclonal antibody or a biological active fragment thereof as defined above, IL-26 specific siRNA oligonucleotide, IL-26 specific antisense oligonucleotide, IL-26 specific shRNA oligonucleotide, IL-26 specific ribozymes oligonucleotide, IL-26 specific Zinc finger nuclease oligonucleotide, dominant negative form of IL-26, or IL-26 aptamers.

Also provided is a pharmaceutical composition comprising the inhibitor of the invention in combination with a pharmaceutically acceptable carrier.

Preferably, the pharmaceutical composition of the invention further comprises one or more of the following: a biologically active substance, a diluent, or an excipient.

The pharmaceutical of the invention is suitable for use in a method of preventing, treating or alleviating the effects of inflammatory diseases selected among the group comprising psoriasis, Crohn's disease, rheumatoid arthritis, ankylosing spondylitis, multiple sclerosis.

Another object of the invention is to provide a kit for the detection and diagnosis of inflammatory-associated diseases and conditions comprising, in one or more containers, the IL-26 inhibitor according to the invention, a detection reagent, and instructions for use.

The invention also contemplates a recombinant IL-26 peptide or IL-26 agonist, for use in the treatment of bacterial infections.

The present invention also discloses methods to treat inflammatory diseases by blocking IL-26, and a screening method to identify IL-26 inhibitors that specifically block the inflammatory function of IL-26.

In particular the present invention relates to the finding of a new inflammatory function of IL-26 (AK155). This function is independent of the known function of IL-26 due to its interaction with the IL-26 receptor expressed selectively on epithelial cells. This interaction, which is the central point of the above-discussed prior art, has not been able to explain the potent inflammatory and pathogenic role of IL-26 producing TH17 cells in chronic inflammatory diseases. The identification of a receptor-independent function that directly acts on immune cells and potently induces immune activation and inflammation now provides an explanation for the potent inflammatory role of Th17 cells and has the following implications:

1) Provides the rational for blocking IL-26 in chronic inflammatory diseases associated with an overexpression of IL-26. Applicants were able to show that in human psoriatic skin IL-26 reaches relevant concentrations for the induction of immune activation and that injection of IL-26 into mouse skin induces a psoriasiform phenotype mediated by the described pathway of immune activation.

2) Provides the basis for developing IL-26 inhibitors/modulators that specifically block the described inflammatory function of IL-26. Applicant have generated anti-human IL-26 antibodies and identified clones that is a strong inhibitor of this function.

Applicants evidenced a unique direct inflammatory role of Th17 cells via production of IL-26 providing the rational for targeting this molecule in diseases where Th17 are implicated in the pathogenesis (e.g. psoriasis, Crohn's, rheumatoid arthritis, ankylosing spondylitis, multiple sclerosis).

BRIEF DESCRIPTION OF THE FIGURES

FIG. 4 (d), IFN-α produced by pDCs stimulated with increasing concentrations of human DNA either alone or in complex with 1 μM IL-26. Data are representative of 3 independent experiments. Error bars represent the standard deviation of triplicate wells.

DETAILED DESCRIPTION OF THE INVENTION

Figure 1A:
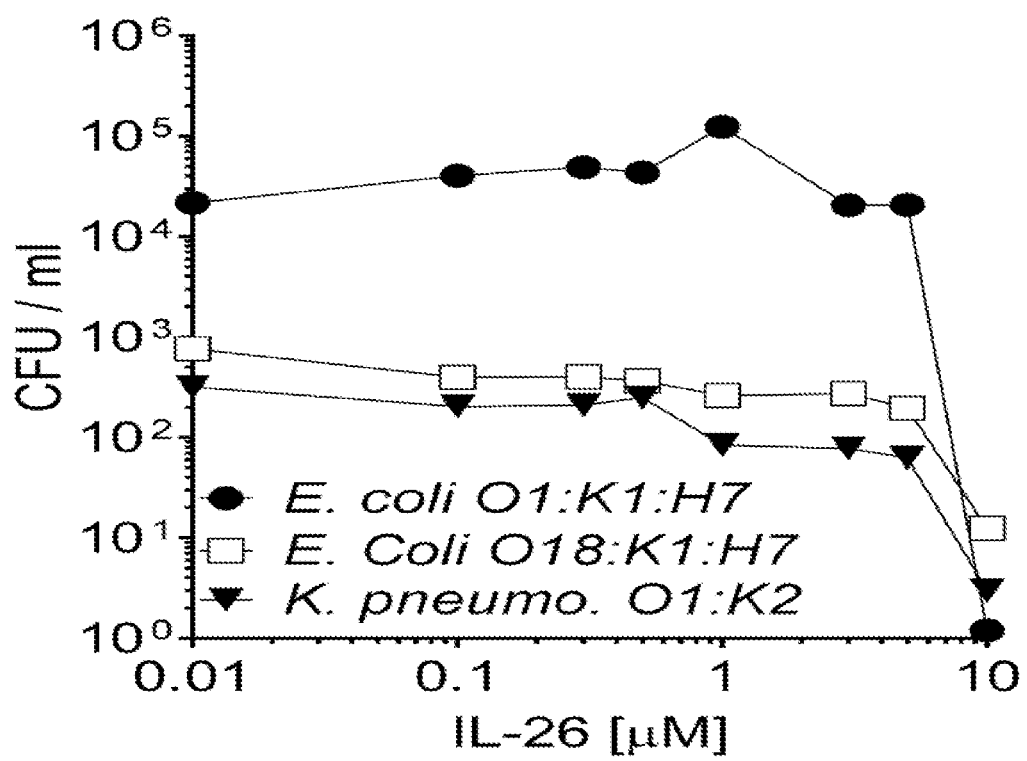
FIG. 1(a). IL-26 has direct bactericidal properties. Growth of *Escherichia coli* O1:K1:H7 (*E. coli*), *E. coli* O18:K1:H7, and *Klebsiella pneumoniae* O1:K2 (*K. pneumo*) in culture with increasing concentration of rhIL-26.

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control.

Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components.

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

The term "monoclonal antibody" is well recognized in the art and refers to an antibody that is the product of a single cloned antibody producing cell. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces the antibody.

By "isolated" is meant a biological molecule free from at least some of the components with which it naturally occurs. An "isolated" antibody is one that has been identified and separated and/or recovered from a component of its natural environment. Contaminant components of its natural environment are materials, which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The terms "antibody" or "antibodies" as used herein are art-recognized terms and are understood to refer to molecules or active fragments of molecules that bind to known antigens, particularly to immunoglobulin molecules and to immunologically active portions of immunoglobulin molecule, i.e molecules that contain a binding site that specifically binds an antigen. An immunoglobulin is a protein comprising one or more polypeptides substantially encoded by the immunoglobulin kappa and lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Also subclasses of the heavy chain are known. For example, IgG heavy chains in humans can be any of IgG1, IgG2, IgG3 and IgG4 subclass. The immunoglobulin according to the invention can be of any class (IgG, IgM, IgD, IgE, IgA and IgY) or subclass (IgG1, IgG2, IgG3, IgG4, IgA1 and IgA2) of immunoglobulin molecule.

As used herein "specifically binds" in reference to an antibody means that the antibody binds to its target antigen with greater affinity that it does to a structurally different antigen(s).

A typical immunoglobulin structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as full length intact antibodies or as a number of well-characterized fragments produced by digestion with various peptidases or chemicals. Thus, for example, pepsin digests an antibody below the disulfide linkages in the hinge region to produce F(ab')2, a dimer of Fab which itself is a light chain joined to VH-CH, by a disulfide bond. The F(ab')2 may be reduced under mild conditions to break the disulfide linkage in the hinge region thereby converting the F(ab')2 dimer into an Fab' monomer. The Fab' monomer is essentially a Fab fragment with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that any of a variety of antibody fragments may be synthesized de novo either chemically or by utilizing recombinant DNA methodology. Thus, the term antibody, as used herein also includes antibody fragments either produced by the modification of whole antibodies or synthesized de novo or antibodies and fragments obtained by using recombinant DNA methodologies.

"Antibodies" are intended within the scope of the present invention to include monoclonal antibodies, polyclonal antibodies, chimeric, single chain, bispecific, simianized, human and humanized antibodies as well as biological active fragments thereof. Examples of biological active fragments of molecules that bind to known antigens include separated light and heavy chains, Fab, Fab/c, Fv, Fab', and F(ab')2 fragments, including the products of an Fab immunoglobulin expression library and epitope-binding fragments of any of the antibodies and fragments mentioned above.

These "biological active fragments" can be derived from an antibody of the present invention by a number of techniques. For example, monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

Recombinant antibodies may be conventional full length antibodies, active antibody fragments known from proteolytic digestion, unique active antibody fragments such as Fv or single chain Fv (scFv), domain deleted antibodies, and the like. An Fv antibody is about 50 Kd in size and comprises the variable regions of the light and heavy chain. A single chain Fv ("scFv") polypeptide is a covalently linked VH::VL heterodimer which may be expressed from a nucleic acid including VH- and VL-encoding sequences either joined directly or joined by a peptide-encoding linker. See Huston, et al. (1988) Proc. Nat. Acad. Sci. USA, 85:5879-5883. A number of structures for converting the naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091,513, 5,132,405 and 4,956,778.

The combining site refers to the part of an antibody molecule that participates in antigen binding. The antigen binding site is formed by amino acid residues of the N-terminal variable ("V") regions of the heavy ("H") and light ("L") chains. The antibody variable regions comprise three highly divergent stretches referred to as "hypervariable regions" or "complementarity determining regions" (CDRs) which are interposed between more conserved flanking stretches known as "framework regions" (FRs). In an antibody molecule, the three hypervariable regions of a light chain (LCDR1, LCDR2, and LCDR3) and the three hypervariable regions of a heavy chain (HCDR1, HCDR2 and HCDR3) are disposed relative to each other in three dimensional space to form an antigen binding surface or pocket. The antibody combining site therefore represents the amino acids that make up the CDRs of an antibody and any framework residues that make up the binding site pocket.

The identity of the amino acid residues in a particular antibody that make up the combining site can be determined using methods well known in the art. For example, antibody CDRs may be identified as the hypervariable regions originally defined by Kabat et al. (see, "Sequences of Proteins of Immunological Interest," E. Kabat et al., U.S. Department of Health and Human Services; Johnson, G and Wu, TT (2001) Kabat Database and its applications: future directions. Nucleic Acids Research, 29: 205-206; http://immuno.bme.nwa.edu). The positions of the CDRs may also be identified as the structural loop structures originally described by Chothia and others, (see Chothia and Lesk, J. Mol. Biol. 196, 901 (1987), Chothia et al., Nature 342, 877 (1989), and Tramontano et al., J. Mol. Biol. 215, 175 (1990)). Other methods include the "AbM definition" which is a compromise between Kabat and Chothia and is derived using Oxford Molecular's AbM antibody modeling software (now Accelrys) or the "contact definition" of CDRs by Macallum et al., ("Antibody-antigen interactions: contact analysis and binding site topography," J Mol Biol. 1996 Oct. 11; 262(5): 732-45). The following chart identifies CDRs based upon various known definitions.

| Loop | Kabat | AbM | Chothia | Contact |
|---|---|---|---|---|
| L1 | L24 -- L34 | L24 -- L34 | L24 -- L34 | L30 -- L36 |
| L2 | L50 -- L56 | L50 -- L56 | L50 -- L56 | L46 -- L55 |
| L3 | L89 -- L97 | L89 -- L97 | L89 -- L97 | L89 -- L96 |
| H1 | H31 -- H35B | H26 -- H35B | H26 -- H32..34 | H30 -- H35B |
| | | (Kabat Numbering) | | |
| H1 | H31 -- H35 | H26 -- H35 | H26 -- H32 | H30 -- H35 |
| | | (Chothia Numbering) | | |
| H2 | H50 -- H65 | H5 -- H58 | H52 -- H56 | H47 -- H58 |
| H3 | H95 -- H102 | H95 -- H102 | H95 -- H102 | H93 -- H101 |

General guidelines by which one may identify the CDRs in an antibody from sequence alone are as follows:

LCDR1:
Start—Approximately residue 24.
Residue before is always a Cys.
Residue after is always a Trp. Typically TRP is followed with TYR-GLN, but also may be followed by LEU-GLN, PHE-GLN, or TYR-LEU.
Length is 10 to 17 residues.
LCDR2:
Start—16 residues after the end of L1.
Sequence before is generally ILE-TYR, but also may be VAL-TYR, ILE-LYS, or ILE-PHE.
Length is generally 7 residues.
LCDR3:
Start—generally 33 residues after end of L2.
Residue before is a Cys.
Sequence after is PHE-GLY-X-GLY.
Length is 7 to 11 residues.
HCDR1:
Start—at approximately residue 26 (four residues after a CYS) [Chothia/AbM definition] Kabat definition starts 5 residues later.
Sequence before is CYS-X-X-X.
Residues after is a TRP, typically followed by VAL, but also followed by ILE, or ALA.
Length is 10 to 12 residues under AbM definition while Chothia definition excludes the last 4 residues.
HCDR2:
Start—15 residues after the end of Kabat/AbM definition of CDR-H1.
Sequence before typically LEU-GLU-TRP-ILE-GLY. (SEQ ID NO. 1), but a number of variations are possible.
Sequence after is LYS/ARG-LEU/ILE/VAL/PHE/THR/ALA-THR/SER/ILE/ALA
Length is 16 to 19 residues under Kabat definition (AbM definition ends 7 residues earlier).
HCDR3:
Start –33 residues after end of CDR-H2 (two residues after a CYS).
Sequence before is CYS-X-X (typically CYS-ALA-ARG).
Sequence after is TRP-GLY-X-GLY.
Length is 3 to 25 residues.

The identity of the amino acid residues in a particular antibody that are outside the CDRs, but nonetheless make up part of the combining site by having a side chain that is part of the lining of the combining site (i.e., it is available to linkage through the combining site), can be determined using methods well known in the art such as molecular modeling and X-ray crystallography. See e.g., Riechmann et al., (1988) Nature, 332: 323-327.

A "conservative amino acid substitution" or "conservative modification" is one in which an amino acid residue is substituted by another amino acid residue having a side chain R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, Methods Mol. Biol. 243:307-31 (1994).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., Science 256:1443-45 (1992), herein incorporated by reference. A "moderately conservative" replacement is any change having a nonnegative value in the PAM250 log-likelihood matrix.

"Chimeric antibodies" are those in which one or more regions of the antibody are from one species of animal and one or more regions of the antibody are from a different species of animal. A preferred chimeric antibody is one which includes regions from a primate immunoglobulin. A chimeric antibody for human clinical use is typically understood to have variable regions from a non-human animal, e.g. a rodent, with the constant regions from a human. In contrast, a humanized antibody uses CDRs from the non-human antibody with most or all of the variable framework regions from and all the constant regions from a human immunoglobulin. A human chimeric antibody is typically understood to have the variable regions from a rodent. A typical human chimeric antibody has human heavy constant regions and human light chain constant regions with the variable regions of both the heavy and light coming from a rodent antibody. A chimeric antibody may include some changes to a native amino acid sequence of the human constant regions and the native rodent variable region sequence. Chimeric and humanized antibodies may be prepared by methods well known in the art including CDR grafting approaches (see, e.g., U.S. Pat. Nos. 5,843,708; 6,180,370; 5,693,762; 5,585,089; 5,530,101), chain shuffling strategies (see e.g., U.S. Pat. No. 5,565,332; Rader et al., Proc. Natl. Acad. Sci. USA (1998) 95:8910-8915), molecular modelling strategies (U.S. Pat. No. 5,639,641), and the like.

A "humanized antibody" as used herein in the case of a two chain antibody is one where at least one chain is humanized. A humanized antibody chain has a variable region where one or more of the framework regions are human. A humanized antibody which is a single chain is one where the chain has a variable region where one or more of the framework regions are human. The non-human portions of the variable region of the humanized antibody chain or fragment thereof is derived from a non-human source, particularly a non-human antibody, typically of rodent origin. The non-human contribution to the humanized antibody is typically provided in form at least one CDR region which is interspersed among framework regions derived from one (or more) human immunoglobulin(s). In addition, framework support residues may be altered to preserve binding affinity.

The humanized antibody may further comprise constant regions (e.g., at least one constant region or portion thereof, in the case of a light chain, and preferably three constant regions in the case of a heavy chain). The constant regions of a humanized antibody if present generally are human.

Methods to obtain "humanized antibodies" are well known to those skilled in the art. (see, e.g., Queen et al., Proc. Natl Acad Sci USA, 86:10029-10032 (1989), Hodgson et al., Bio/Technology, 9:421 (1991)).

A "humanized antibody" may also be obtained by a novel genetic engineering approach that enables production of affinity-matured human-like polyclonal antibodies in large animals such as, for example, rabbits and mice. See, e.g. U.S. Pat. No. 6,632,976.

The term constant region (CR) as used herein refers to constant regions genes of the immunoglobulin. The constant region genes encode the portion of the antibody molecule which confers effector functions. For Chimeric human antibodies and humanized antibodies, typically non-human (e.g., murine), constant regions are substituted by human constant regions. The constant regions of the subject chimeric or humanized antibodies are typically derived from human immunoglobulins. The heavy chain constant region can be selected from any of the five isotypes: alpha, delta, epsilon, gamma or mu. Further, heavy chains of various subclasses (such as the IgG subclasses of heavy chains) are responsible for different effector functions and thus, by choosing the desired heavy chain constant region, antibodies with desired effector function can be produced. Constant regions that may be used within the scope of this invention are gamma 1 (IgG1), particularly an Fc region of the gamma 1 (IgG1) isotype, gamma 3 (IgG3) and especially gamma 4 (IgG4). The light chain constant region can be of the kappa or lambda type, preferably of the kappa type. In one embodiment the light chain constant region is the human kappa constant chain (Heiter et al. (1980) Cell 22:197-207) and the heavy constant chain is the human IgG4 constant chain.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc and/or Fv fragments. The term "antigen-binding fragment" refers to a polypeptide fragment of an immunoglobulin or antibody that binds antigen or competes with intact antibody (i.e., with the intact antibody from which they were derived) for antigen binding (i.e., specific binding).

Binding fragments are produced by recombinant DNA techniques, or by enzymatic or chemical cleavage of intact immunoglobulins. Binding fragments include Fab, Fab', F(ab')2, Fabc, Fv, single chains, and single-chain antibodies.

The term "antigen" refers to an entity or fragment thereof which can bind to an antibody. An immunogen refers to an antigen which can elicit an immune response in an organism, particularly an animal, more particularly a mammal including a human. The term antigen includes regions known as antigenic determinants or epitopes which refers to a portion of the antigen (which are contacted or which play a significant role in supporting a contact reside in the antigen responsible for antigenicity or antigenic determinants.

As used herein, the term "epitope" refers to a portion of an antigenic molecule to which an antibody is produced and to which the antibody will bind. Epitopes can comprise linear amino acid residues (i.e., residues within the epitope are arranged sequentially one after another in a linear fashion), nonlinear amino acid residues, or both linear and nonlinear amino acid residues. Typically epitopes are generally short amino acid sequences (e.g. about five amino acids in length).

Also as used herein, the term "immunogenic" refers to substances which elicit the production of antibodies, recruitment of T-cells and other reactive immune cells directed against an antigen of the immunogen.

An immune response occurs when an individual produces sufficient antibodies, T-cells and other reactive immune cells against administered immunogenic compositions of the present invention to moderate or alleviate the disorder to be treated.

The term immunogenicity as used herein refers to a measure of the ability of an antigen to elicit an immune response (humoral or cellular) when administered to a recipient. The present invention is concerned with approaches that reduce the immunogenicity of the subject human chimeric or humanized antibodies.

The language "diseases and disorders which are caused by or associated with IL-26" includes, but is not limited to, inflammatory diseases or disorders selected among the group comprising psoriasis, Crohn's disease, rheumatoid arthritis, ankylosing spondylitis, multiple sclerosis.

As used herein the terms "subject" or "patient" or "beneficiary" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject. The term does not denote a particular age or sex. Thus, young, adult and new-born subjects, whether male or female, are intended to be covered.

The term "an effective amount" refers to an amount necessary to obtain a physiological effect. The physiological effect may be achieved by one application dose or by repeated applications. The dosage administered may, of course, vary depending upon known factors, such as the physiological characteristics of the particular composition; the age, health and weight of the subject; the nature and extent of the symptoms; the kind of concurrent treatment; the frequency of treatment; and the effect desired and can be effectively adjusted by a person skilled in the art.

"Inflammation" is part of the complex biological response of vascular tissues to harmful stimuli, such as pathogens, damaged cells, or irritants. The inflammatory response enables a subject to immediately detect and destroy infection or toxic material in damaged tissue before it can spread to other areas of the body. Inflammation develops as a normal protective response of the immune system when body tissue is irritated. When tissue is irritated, the immune system increases blood flow to the area, which causes localized swelling, warmth, and redness. Inflammation may occur anywhere in the body, and may occur with overuse of a body area or with minor injuries.

Inflammation is a protective attempt by the organism to remove the injurious stimuli and to initiate the healing process. Inflammation is not a synonym for infection, even in cases where inflammation is caused by infection.

Although infection is caused by a microorganism, inflammation is one of the responses of the organism to the pathogen. However, inflammation can be considered as a mechanism of innate immunity as compared to adaptive immunity, which is specific for each pathogen.

The term "inflammatory diseases" refers to a group of diseases and disorders associated with the expression of IL-26 including, but not limited to psoriasis, Crohn's disease, rheumatoid arthritis, ankylosing spondylitis, multiple sclerosis.

It also refers to other diseases associated with inflammation including but not limited to insulin-dependent diabetes mellitus (IDDM), diabetes mellitus, multiple sclerosis, acute disseminated encephalomyelitis, myasthenia gravis, thyroiditis, uveoretinitis, Hashimoto's disease, primary myxoedema, thyrotoxicosis, pernicious anaemia, autoimmune atrophic gastritis, Addison's disease, premature menopause, male infertility, juvenile diabetes, Goodpasture's syndrome, pemphigus vulgaris, pemphigoid, sympathetic ophthalmia, phacogenic uveitis, autoimmune haemolytic anaemia, idiopathic leucopenia, primary biliary cirrhosis, active chronic hepatitis Hbs-ve, cryptogenic cirrhosis, ulcerative colitis, Sjogren's syndrome, scleroderma, Wegener's granulomatosis, Poly/Dermatomyositis, discoid LE, systemic Lupus erythematosus, Antiphospholipid antibody syndrome, Aplastic anemia, Autoimmune hepatitis, Coeliac disease, Graves' disease, Guillain-Barré syndrome (GBS), Idiopathic thrombocytopenic purpura, Opsoclonus myoclonus syndrome (OMS), Optic neuritis, Ord's thyroiditis, Pemphigus, Polyarthritis, Primary biliary cirrhosis, Rheumatoid arthritis, Reiter's syndrome, Takayasu's, Temporal arteritis, Warm autoimmune hemolytic anemia, Wegener's granulomatosis, Alopecia universalis, Behcet's disease, Chagas' disease, Chronic fatigue syndrome, Dysautonomia, Endometriosis, Hidradenitis suppurativa, Interstitial cystitis, Neuromyotonia, Sarcoidosis, Scleroderma, Ulcerative colitis, Vitiligo, and Vulvodynia.

The culture medium in which the hybridoma cells are cultured can then be assayed for the presence of monoclonal antibodies directed against IL-26 or a fragment thereof. The binding specificity of monoclonal antibodies produced by the hybridoma cells can be determined by inmunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard (1980) Anal. Biochem. 107:220.

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures, such as, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

One aspect of the invention is a purified and isolated monoclonal antibody (also referred herein as IL-26 antibody) or a biological active fragment thereof that specifically recognizes and binds IL-26, wherein said monoclonal antibody or fragment thereof comprises:
  i) a Heavy Chain Variable Region (HCVR), and
  ii) a Light Chain Variable Region (LCVR).

Said isolated monoclonal antibody or biological active fragment thereof, comprises: a heavy chain variable region that comprises CDR1, CDR2, CDR3 sequences and a light chain variable region that comprises CDR1, CDR2, CDR3 sequences and conservative modifications thereof.

It is thus one object of the present invention to provide an isolated monoclonal antibody or biological active fragment thereof that recognizes and binds IL-26, comprising: a heavy chain variable region that comprises CDR1, CDR2, CDR3 sequences and a light chain variable region that comprises CDR1, CDR2, CDR3 sequences wherein:

(a) the heavy chain variable region CDR1 sequence comprises the amino acid sequence of SEQ ID NOs: 5 or conservative modifications thereof;

(b) the heavy chain variable region CDR2 sequence comprises the amino acid sequence of SEQ ID NOs: 6 or conservative modifications thereof;

(c) the heavy chain variable region CDR3 sequence comprises the amino acid sequence of SEQ ID NOs: 7 or conservative modifications thereof;

(d) the light chain variable region CDR1 sequence comprises the amino acid sequence of SEQ ID Nos 8 or conservative modifications thereof;

(e) the light chain variable region CDR2 sequence comprises the amino acid sequence of SEQ ID Nos 9 or conservative modifications thereof;

(f) the light chain variable region CDR3 sequence comprises the amino acid sequence of SEQ ID Nos 10 or conservative modifications thereof.

Preferably the isolated monoclonal antibody or the biological active fragment thereof capable of recognizing and specifically binding IL-26 comprises:
  i) a Heavy Chain Variable Region (HCVR) comprising the amino acid sequence of SEQ ID NO:3, and
  ii) a Light Chain Variable Region (LCVR) comprising the amino acid sequence of SEQ ID NO:4.

More preferably, the isolated monoclonal antibody or biological active fragment thereof capable of recognizing and binding IL-26 consists of:
  a heavy chain comprising the amino acid sequence of SEQ ID NO: 3 and a light chain comprising the amino acid sequence of SEQ ID NO: 4.

Also provided is a nucleic acid molecule comprising a nucleotide sequence encoding the monoclonal antibody or a biological active fragment thereof.

Preferably the nucleic acid molecule comprises the nucleotide sequence of SEQ ID NO: 1 encoding for the heavy chain of the monoclonal antibody and/or the nucleotide sequence of SEQ ID NO: 2 encoding for the light chain of the monoclonal antibody of the invention.

It is another object of the invention to provide an expression vector comprising the nucleotide acid molecule of the invention.

A further object of the invention is a cell comprising the expression vector of the invention.

It is yet a further object of the present invention to provide for a hybridoma and an isolated monoclonal antibody secreted by said hybridoma.

Consequently the present invention concerns a mouse hybridoma cell line deposited under an ATCC accession number PTA-122358 and filed on Jul. 10, 2015 with the ATCC.

It is another object of the invention to provide a monoclonal antibody that recognizes and binds IL-26 and having the same epitope specificity as the monoclonal antibody produced by hybridoma cell line 142-84-B1, ATCC accession number PTA-122358.

In an embodiment of the invention, it is provided an isolated monoclonal antibody that recognizes and binds IL-26, and wherein said isolated monoclonal antibody is produced by hybridoma cell line 142-84-B1, ATCC accession number PTA-122358.

Also provided is a pharmaceutical composition comprising the isolated monoclonal antibody or the biological active fragment thereof according to the invention, and optionally further comprising a pharmaceutically acceptable carrier.

Preferably, the pharmaceutical composition of the invention further comprises one or more of the following: a biologically active substance, a diluent, or an excipient.

In another embodiment of the invention, the isolated monoclonal antibody or the biological active fragment thereof and/or the pharmaceutical composition containing the same is suitable for use in the treatment or alleviation of the effects of inflammatory diseases selected among the group comprising psoriasis, Crohn's disease, rheumatoid arthritis, ankylosing spondylitis, multiple sclerosis, insulin-dependent diabetes mellitus (IDDM), diabetes mellitus, multiple sclerosis, acute disseminated encephalomyelitis, myasthenia gravis, thyroiditis, uveoretinitis, Hashimoto's disease, primary myxoedema, thyrotoxicosis, pernicious anaemia, autoimmune atrophic gastritis, Addison's disease, premature menopause, male infertility, juvenile diabetes, Goodpasture's syndrome, pemphigus vulgaris, pemphigoid, sympathetic ophthalmia, phacogenic uveitis, autoimmune haemolytic anaemia, idiopathic leucopenia, primary biliary cirrhosis, active chronic hepatitis Hbs-ve, cryptogenic cirrhosis, ulcerative colitis, Sjogren's syndrome, scleroderma, Wegener's granulomatosis, Poly/Dermatomyositis, discoid LE, systemic Lupus erythematosus, Antiphospholipid antibody syndrome, Aplastic anemia, Autoimmune hepatitis, Coeliac disease, Graves' disease, Guillain-Barré syndrome (GBS), Idiopathic thrombocytopenic purpura, Opsoclonus myoclonus syndrome (OMS), Optic neuritis, Ord's thyroiditis, Pemphigus, Polyarthritis, Primary biliary cirrhosis, Rheumatoid arthritis, Reiter's syndrome, Takayasu's, Temporal arteritis, Warm autoimmune hemolytic anemia, Wegener's granulomatosis, Alopecia universalis, Behcet's disease, Chagas' disease, Chronic fatigue syndrome, Dysautonomia, Endometriosis, Hidradenitis suppurativa, Interstitial cystitis, Neuromyotonia, Sarcoidosis, Scleroderma, Ulcerative colitis, Vitiligo, and Vulvodynia.

Preferably the inflammatory diseases are selected among the group comprising psoriasis, Crohn's disease, rheumatoid arthritis, ankylosing spondylitis, multiple sclerosis.

Preferably, the pharmaceutical composition, further comprises one or more of the following: a biologically active substance, a diluent, or an excipient.

More preferably, the active substance is a compound used in the treatment of inflammatory diseases such as psoriasis.

Even more preferably, the compound is selected among the list comprising: methotrexate, cyclosporin, fumaric acid, Neotigason; TNF blockers selected among etanarcept, adalimumab, infliximab; IL-12/23p40 blockers such as ustekinumab; Anti-IL-17 antibodies selected among secukinumab, ixekinumab; Apremilast, tofacitinib.

The monoclonal antibody or the biological active fragment thereof and/or the pharmaceutical composition of the invention is used in the treatment or alleviation of the effects of inflammatory diseases selected among the group comprising psoriasis, Crohn's disease, rheumatoid arthritis, ankylosing spondylitis, multiple sclerosis.

In particular, the treatment of the patient with the monoclonal antibody of the invention, leads to a decrease in the:
 a—Lesional type I IFN production (IFN-a or IFN-b) and decrease of type I IFN induced gene expression;
 b—cell infiltration and the expression of the inflammatory genes IL-6, TNF, IL-12, IL-23, IL-8, IL-17, IL-22, IFN-g.

More preferably the treatment of psoriasis in a patient, with the monoclonal antibody of the invention further leads to a decrease in the:
 i—epidermal thickening on histology (acanthosis and papillomatosis) and the clinical resolution of the plaque
 ii—the PASI score.

In a further aspect of the invention it is provided an inhibitor of the expression or activity of IL-26, for use in the treatment or alleviation of the effects of inflammatory diseases, wherein said inhibitor of the expression or activity of IL-26 is selected among the group comprising, the IL-26 monoclonal antibody or a biological active fragment thereof as described above, IL-26 specific siRNA oligonucleotide, IL-26 specific antisense oligonucleotide, IL-26 specific shRNA oligonucleotide, IL-26 specific ribozymes oligonucleotide, IL-26 specific Zinc finger nuclease oligonucleotide, dominant negative form of IL-26, or IL-26 aptamers.

Other IL-26 inhibitors or IL-26 modulators may be used in accordance with the spirit of the present invention. Inhibition of the expression or the activity of IL-26 may be achieved by any technique known to the skilled in the art.

For the sake of clarity, the following techniques are described as follows:

Aptamers:

Aptamers are single-stranded DNA or RNA (ssDNA or ssRNA) molecules generated from large random libraries by an iterative process called Systematic Evolution of Ligands by Exponential Enrichment (SELEX). There are small in size (15-60 nucleotides in length) and can assume a variety of shapes due to their propensity to form helices and single-stranded loops, explaining their versatility in binding to diverse targets (such as a protein). Due to their high versatility, aptamers have a higher affinity to their targets compared to antibodies. The fact that aptamers can be produced by chemical synthesis eliminates batch-to-batch and makes it attractive for clinical applications. Aptamers identified by SELEX can also be easily analyzed and manipulated to characterize the minimum sequence requirements for target-ligand recognition. Their specificity and characteristics are not directly determined by their primary sequence, but instead by their tertiary structure. Some 20 or more aptamers compounds are in various stages of clinical trials for a variety of indications; the eyetech's Macugen was approved by FDA in 2004 for the treatment of wet age-related macular degeneration (AMD) (www.clinicaltrials.gov).

Zinc Finger Nuclease (ZFN):

A ZEN is a hybrid molecule that couples the DNA binding domain of a zinc-finger protein with the DNA-cleaving nuclease domain of the restriction endonuclease Fokl. The DNA binding motif specified by the zinc fingers directs the ZFN to a specific (targeted) locus in the genome. A pair of ZFNs is required to cleave double-stranded DNA. Each ZEN recognizes a different 12-18 base pair target sequence, and these target sequences must be separated by 4-7 base pairs to allow formation of the catalytically active Fokl dimer. These positional constraints drive a very high degree of specificity.

Ribozymes can also function as inhibitors of expression of IL-26 for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of IL-26 mRNA sequences are thereby useful within the scope of the present invention. Specific ribozyme cleavage sites within any potential RNA target are initially identified by scanning the target molecule for ribozyme cleavage sites, which typically include the following sequences, GUA, GuU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

siRNA:

siRNA is formed in the cell from shRNA or from long synthetic dsRNA by the Dicer enzyme, and is later separated into two short strands, one of which binds to the target mRNA and cleaves it, preventing the unwanted protein from being made. In the siRNA approach, specific siRNAs are synthesized in the laboratory to silence specific proteins in target cells which are implicated in disease.

shRNA:

shRNA is short hairpin RNA, double stranded RNA (dsRNA) which is created in the cell from a DNA construct encoding a sequence of single stranded RNA and its complement, separated by a stuffer fragment, allowing the RNA molecule to fold back on itself, creating a dsRNA molecule with a hairpin loop. The target cell can be directed to produce shRNA by specific DNA sequences introduced to the cell via a small gene cassette which travels to the nucleus. Here the introduced DNA either becomes part of the cell's own DNA or persists in the nucleus, and instructs the cell to produce the specific shRNA, which is then processed by Dicer to siRNA and continues along the RNAi pathway via RISC to silence the gene.

Dominant Negative Form of IL-26:

a dominant negative form of IL-26, termed Ac—IL-26, has been created by replacing the basic DNA binding region of IL-26 with an acidic region while retaining the leucine zipper. Retroviruses or lentiviruses can be used to transduce Ac—IL-26 into cells.

Chemical inhibitors of IL-26. Some chemical inhibitors can increase the degradation of IL-26 in cells. Those chemical inhibitors can be identified by using the screening method of the invention.

The inflammatory diseases are selected among the group comprising psoriasis, Crohn's disease, rheumatoid arthritis, ankylosing spondylitis, multiple sclerosis, insulin-dependent diabetes mellitus (IDDM), diabetes mellitus, multiple sclerosis, acute disseminated encephalomyelitis, myasthenia gravis, thyroiditis, uveoretinitis, Hashimoto's disease, primary myxoedema, thyrotoxicosis, pernicious anaemia, autoimmune atrophic gastritis, Addison's disease, premature menopause, male infertility, juvenile diabetes, Goodpasture's syndrome, pemphigus vulgaris, pemphigoid, sympathetic ophthalmia, phacogenic uveitis, autoimmune haemolytic anaemia, idiopathic leucopenia, primary biliary cirrhosis, active chronic hepatitis Hbs-ve, cryptogenic cirrhosis, ulcerative colitis, Sjogren's syndrome, scleroderma, Wegener's granulomatosis, Poly/Dermatomyositis, discoid LE, systemic Lupus erythematosus, Antiphospholipid antibody syndrome, Aplastic anemia, Autoimmune hepatitis, Coeliac disease, Graves' disease, Guillain-Barré syndrome (GBS), Idiopathic thrombocytopenic purpura, Opsoclonus myoclonus syndrome (OMS), Optic neuritis, Ord's thyroiditis, Pemphigus, Polyarthritis, Primary biliary cirrhosis, Rheumatoid arthritis, Reiter's syndrome, Takayasu's, Temporal arteritis, Warm autoimmune hemolytic anemia, Wegener's granulomatosis, Alopecia universalis, Behcet's disease, Chagas' disease, Chronic fatigue syndrome, Dysautonomia, Endometriosis, Hidradenitis suppurativa, Interstitial cystitis, Neuromyotonia, Sarcoidosis, Scleroderma, Ulcerative colitis, Vitiligo, and Vulvodynia.

Preferably the inflammatory diseases are selected among the group comprising psoriasis, Crohn's disease, rheumatoid arthritis, ankylosing spondylitis, multiple sclerosis.

It has been observed that the treatment of the effects of inflammatory diseases in a patient with the inhibitor of the invention, leads to a decrease in the:

a—Lesional type I IFN production (IFN-a or IFN-b) and decrease of type I IFN induced gene expression;

b—cell infiltration and the expression of the inflammatory genes IL-6, TNF, IL-12, IL-23, IL-8, IL-17, IL-22, IFN-g.

In particular, when it concerns the treatment of psoriasis in a patient, the treatment with the inhibitor of the invention further leads to a decrease in the:

i—epidermal thickening on histology (acanthosis and papillomatosis) and the clinical resolution of the plaque ii—the PASI score.

Also provided is a pharmaceutical composition comprising the inhibitor of the invention in combination with a pharmaceutically acceptable carrier.

In other embodiments there is provided a pharmaceutical composition including the monoclonal antibody or biological active fragment thereof as described above together with a pharmaceutically acceptable carrier, diluent or excipient.

In the preparation of the pharmaceutical compositions comprising the antibodies described in the teachings herein, a variety of vehicles and excipients and routes of administration may be used, as will be apparent to the skilled artisan. Representative formulation technology is taught in, inter alia, Remington: The Science and Practice of Pharmacy, 19th Ed., Mack Publishing Co., Easton, Pa. (1995) and Handbook of Pharmaceutical Excipients, 3rd Ed, Kibbe, A. H. ed., Washington D.C., American Pharmaceutical Association (2000); hereby incorporated by reference in their entirety.

The pharmaceutical compositions will generally comprise a pharmaceutically acceptable carrier and a pharmacologically effective amount of the antibodies, or mixture of antibodies.

The pharmaceutical composition may be formulated as powders, granules, solutions, suspensions, aerosols, solids, pills, tablets, capsules, gels, topical creams, suppositories, transdermal patches, and other formulations known in the art.

For the purposes described herein, pharmaceutically acceptable salts of the antibodies are intended to include any art-recognized pharmaceutically acceptable salts including organic and inorganic acids and/or bases. Examples of salts include sodium, potassium, lithium, ammonium, calcium, as well as primary, secondary, and tertiary amines, esters of lower hydrocarbons, such as methyl, ethyl, and propyl. Other salts include organic acids, such as acetic acid, propionic acid, pyruvic acid, maleic acid, succinic acid, tartaric acid, citric acid, benzoic acid, cinnamic acid, salicylic acid, etc.

As used herein, "pharmaceutically acceptable carrier" comprises any standard pharmaceutically accepted carriers known to those of ordinary skill in the art in formulating pharmaceutical compositions. Thus, the antibodies or peptides, by themselves, such as being present as pharmaceutically acceptable salts, or as conjugates, may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or as solid formulations in appropriate excipients.

The pharmaceutical compositions will often further comprise one or more buffers (e.g., neutral buffered saline or phosphate buffered saline), carbohydrates (e.g., glucose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, adjuvants (e.g., aluminium hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

While any suitable carrier known to those of ordinary skill in the art may be employed in the compositions of this invention, the type of carrier will typically vary depending on the mode of administration. Antibody compositions may be formulated for any appropriate manner of administration, including for example, oral, nasal, mucosal, intravenous, intraperitoneal, intradermal, subcutaneous, and intramuscular administration.

For parenteral administration, the compositions can be administered as injectable dosages of a solution or suspension of the substance in a physiologically acceptable diluent with a pharmaceutical carrier that can be a sterile liquid such as sterile pyrogen-free water, oils, saline, glycerol, polyethylene glycol, or ethanol. Additionally, auxiliary substances, such as wetting or emulsifying agents, surfactants, pH buffering substances and the like can be present in compositions.

Other components of pharmaceutical compositions are those of petroleum, animal, vegetable, or synthetic origin, for example, non-aqueous solutions of peanut oil, soybean oil, corn oil, cottonseed oil, ethyl oleate, and isopropyl myristate. Antibodies can be administered in the form of a depot injection or implant preparation, which can be formulated in such a manner as to permit a sustained release of the active ingredient. An exemplary composition comprises antibody at 5 mg/ml, formulated in aqueous buffer consisting of 50 mM L-histidine, 150 mM NaCl, adjusted to pH 6.0 with HCl.

Typically, the compositions are prepared as injectables, either as liquid solutions or suspensions; solid or powder forms suitable for reconstitution with suitable vehicles, including by way example and not limitation, sterile pyrogen free water, saline, buffered solutions, dextrose solution, etc., prior to injection. The preparation also can be emulsified or encapsulated in liposomes or micro particles such as polylactide, polyglycolide, or copolymers.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles, as indicated above.

Alternatively, a pharmaceutical composition may be stored in a freeze-dried condition requiring only the addition of a sterile liquid carrier immediately prior to use.

Preferably, the pharmaceutical composition of the invention further comprises one or more of the following: a biologically active substance, a diluent, or an excipient.

More preferably the biologically active substance is a compound used in the treatment of inflammatory diseases such as psoriasis.

For the treatment of psoriasis, said compound is selected among the list comprising: methotrexate, cyclosporin, fumaric acid, Neotigason; TNF blockers selected among etanarcept, adalimumab, infliximab; IL-12/23p40 blockers such as ustekinumab; anti-IL-17 antibodies selected among secukinumab, ixekinumab; Apremilast, tofacitinib.

The pharmaceutical of the invention is therefore suitable for use in a method of preventing, treating or alleviating the effects of inflammatory diseases selected among the group comprising psoriasis, Crohn's disease, rheumatoid arthritis, ankylosing spondylitis, multiple sclerosis.

Another object of the invention is to provide a kit for detection and diagnosis of inflammatory-associated diseases and conditions comprising, in one or more containers, the IL-26 inhibitor or the monoclonal antibody or biological active fragment thereof according to the invention, a detection reagent, and instructions for using the antibodies or inhibitors of the invention.

In particular, antibody kits are provided which contain the necessary reagents to carry out the assays of the present invention. The kit may include one or more compartments, each to receive one or, more containers such as: (a) a first container comprising one of the components of the present invention described above; and (b) one or more other containers comprising one or more of the following: wash reagents, reagents capable of detecting presence of the antibody or biological active fragments thereof as a control for detection or for a competitive assay.

The containers allow one to efficiently transfer reagents from one compartment to another compartment such that the samples and reagents are not cross-contaminated, and the agents or solutions of each container can be added in a quantitative fashion from one compartment to another.

The kit typically contains containers, which may be formed from a variety of materials such as glass or plastic, and can include for example, bottles, vials, syringes, and test tubes. A label typically accompanies the kit, and includes any writing or recorded material, which may be electronic or computer readable form (e.g., disk, optical disc, or tape) providing instructions or other information for used of the contents of the kit. The label indicates that the formulation is used for diagnosing or treating the disorder of choice according to the present invention. One skilled in the art will readily recognize that the disclosed antibodies of the present invention can be readily incorporated into one of the established kit formats, which are well known in the art.

The invention also contemplates a recombinant IL-26 peptide or IL-26 agonist, for use in the treatment of bacterial infections.

It is yet another object of the present invention to provide for a method for screening of IL-26 inhibitors comprising:

A) Inhibition of the inflammatory activity of IL-26 (antibodies, aptamers, small molecules): A pDC activation protocol with IL-26-DNA complexes was performed. Briefly, IL-26-DNA complexes are generated by mixing 600 ng of human DNA (BioChain) with recombinant IL-26 in 40 µl of nuclease-free water (Ambion) and then are diluted into 200 µl of complete medium for pDC stimulation (final concentrations: 3 µg/ml DNA and 1 µM IL-26). Increasing concentrations of the inhibitor is added into the final cultures. IFN-α are measured in the supernatants of pDC after overnight culture.

B) Inhibition of IL-26 expression (siRNA, shRNA, antisense, small molecules):

Inhibitors are added during restimulation of TH17 clones or primary TH17 cells with aCD3 and 1CD28. Supernatants are then tested on pDC for their ability to induce IFN-a production.

The pharmaceutical composition of the invention is suitable for use in a method of preventing, treating or alleviating the effects of inflammatory diseases selected among the group comprising psoriasis, Crohn's disease, rheumatoid arthritis, ankylosing spondylitis, multiple sclerosis.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practising the present invention and are not intended to limit the scope of the invention.

EXAMPLES

Material and Methods

Human Samples

Studies were approved by the institution review board of the University of Texas MD Anderson Cancer Center, the Heinrich-Heine University of Dusseldorf, and the University of Lausanne, and performed in accordance with the guidelines of the Declaration of Helsinki Skin punch biopsies were taken, after obtaining informed consent, from patients suffering from plaque psoriasis defined according to standard clinical and histophathological criteria as well as healthy donors. Samples were snap-frozen, and stored at −80° C. Blood buffy coats of healthy donors were obtained from the Gulf Coast Regional Blood Center, Houston, Tex. or from the Service Vaudois de Transfusion, Epalinges, Switzerland.

Reagents

Recombinant human IL-26 (rhIL-26), rhIL-17, and rhIL-22 were from R&D Systems. Human genomic DNA (huDNA) isolated from fetal skin, lung or leucocytes was purchased from BioChain. Synthetic LL-37 and hBD3 were purchased from Innovagen. Antibodies against IL-26 were generated by immunizing 6-8-wk-old BALB/c mice with rhIL-26 protein. Hybridomas secreting antibodies specific for IL-26 were established. Two clones we used in these studies: clone 142-84-B1 with the ability to inhibit binding of IL-26 to DNA, and clone 142-69-1 with the ability to stain IL-26 for confocal microscopy. Both clones were used at 10 µg/ml. Mouse IgG1 isotype-matched antibodies were used as controls. Synthetic phosphothioate TLR9 agonist CpG-2006 (1 µM) (5'-tcgtcgttttgtcgttttgtcgtt-3') was purchased from Trilink. The TLR1/2 agonist Pam3CSK4, the TLR2 agonist LTA and the TLR4 agonist LPS were purchased from Invivogen. Blocking goat anti-human IL-10R2 antibodies was from R&D systems. Chloroquine was purchased from Sigma.

Protein Modeling

The human IL-26 models (Uniprotkp sequence Q9NPH9) were generated using the software i-Tasser. Further modeling of IL-26 was based on the published atomic structures of IL-19 (PDB entry 1N1F) and IL-22 (1M4R), whereas a putative arm-exchanged IL-26 model was based on the atomic structure of IL-10 (2ILK). The sequences of IL-19, IL-22 and IL-10 are about 25% identical and about 55% similar to IL-26. The best i-Tasser model (a compact monomer) had a high significance C-score of 0.36, with an expected rmsd of 4.0±2.7 Å.

Small Angle X-Ray Scattering (SAXS)

IL-26 was suspended in 16 mM sodium phosphate buffer, pH 6.5, 560 mM NaCl, 8% glycerol, 2 mM β-mercaptoethanol and concentrated to 1.1 mg/ml. Data were recorded at the ALS, Berkeley, Calif., beamline 12.3.1. (SIBYLS) at 10° C. using a wavelength of 1 Å, for values of the momentum transfer vector $q=(4\pi \sin \theta)/\lambda$ between 0.01 and 0.32 Å-1. The same sample was sequentially exposed to X-rays for 0.5 s, 1 s and 5 s. Samples containing buffer only were measured before and after protein samples. The buffer contributions were subtracted from protein scattering data using the ogre new software program available at SIBYLS. Data were not affected by radiation damage as indicated by a constant Rg of the Guinier region for subsequent sample exposures. A combined SAXS pattern was obtained through scaling and merging selected regions of buffer-subtracted scattering pattern for the 0.5 s, 1 s and 5 s exposures. Data between q=0.01 and 0.13 Å-1 were analyzed using PRIMUS, SASREF and DAMMIF of the ATSAS software package.

Antimicrobial Assays

The following bacteria strains were used *Pseudomonas aeruginosa* (ATCC27853 and PA14), *Escherichia coli* (O1: K1:H7, O18:K1:H7, O111:K58:H2 and J5 O111:B4), *Staphylococcus aureus* (ATCC6538), *Klebsiella pneumoniae* O1:K2, *Enterococcus faecalis* (ATCC29212). Bacteria were cultured overnight in trypticase soy broth (TB)+10 mM NaCl at 37° C. followed by subculturing for additional 3 h to obtain mid logarithmic-phase growth. Bacterial concentrations were measured by spectrophotometry at 620 nm and diluted to provide a final concentration of 105 colony forming units (CFU)/ml, followed by 24 h incubation at 37° C. under low ionic strength conditions (10 mM NaCl). Effects of IL-26, LL-37 or hBD3 were added to these cultures to test their antimicrobial activity. After 24 h, serial dilutions of bacterial cultures were plated onto (Lysogeny broth) LB agar plates. The number of colonies formed after overnight incubation was counted by two independent investigators. The minimum inhibitory concentration 50 (MIC50) of IL-26 was defined as the lowest concentration that inhibited >50% of the growth of bacteria after overnight incubation. In some experiments, bacteria were incubated in antibiotics-free RPMI medium or TH17 supernatants supplemented or not with the blocking anti-IL-26 clone 142-84-1 at 10 µg/ml. For analysis of the membrane potential loss, bacteria were incubated with 10 µM IL-26 and harvested at different time points to be stained with the fluorescent membrane-potential indicator dye DiOC2(3) (BacLight bacterial membrane potential kit, Molecular Probes) according to the manufacturer's protocol. As a positive control, 5 µM CCCP, a proton ionophore was used. For further analysis of the bacterial death, bacterial nucleic acids were stained by 5 µM of the cell permeant SYTO® 13 Green dye and 5 µM of the cell impermeant SYTOX® Orange dye (Life technologies). All viable bacteria will be stained by SYTO® 13 Green but not SYTOX® Orange whereas dead bacteria will be stained with both dyes.

Scanning Electron Microscopy of *Pseudomonas aeruginosa*

$5 \times 10^5$ CFU *Pseudomonas aeruginosa* were incubated with IL-26 or vehicle (Sodium phosphate, 1.0 M NaCl, 10% glycerol, pH 6.5) for 30 to 180 min in TB. Samples were placed on poly-1-lysine treated glass coverslips and allowed to dry overnight. Samples on coverslips were mounted on to double-stick carbon tabs (Ted Pella. Inc.), which have been previously mounted on to aluminum specimen mounts (Electron Microscopy Sciences). The samples were then coated under vacuum using a Balzer MED 010 evaporator (Technotrade International) with platinum alloy for a thickness of 25 nm, then immediately flash carbon coated under vacuum. The samples were transferred to a desiccator for examination at a later date. Samples were examined in a JSM-5910 scanning electron microscope (JEOL, USA, Inc.) at an accelerating voltage of 5 kV.

ELISA Binding Assay

Nunc MaxiSorp® 96-well plates were coated with PBS 1% BSA, 1 µg/ml LPS or 1 µg/ml LTA for 24 hours at 4° C. Plates were then washed and increasing concentrations of IL-26, LL-37 or IL-22 diluted in PBS 1% BSA were added for 1 hour at RT. Plates were then washed and 0.5 µg/ml of mouse anti-IL-26 (Clone 142-69-1), anti-LL-37 (Santa Cruz) or anti-IL-22 (RnD systems) antibodies diluted in PBS 1% BSA were added for 1 hour at RT. Plates were then washed and goat anti-mouse IgG-HRP (Thermo scientific) diluted 1/5000 in PBS 1% BSA was added to all wells for 30 min at RT. Plates were then washed and TMB substrate was added. Plates were then read at 450 nm using a spectrometer.

In Vivo Lung Infection Model

Animal procedures were approved by the "Office Vétérinaire du Canton de Vaud", Lausanne, Switzerland and performed according to the federal guidelines for animal experimentation. *Klebsiella pneumoniae* strain Caroli (O1: K2) 22 was cultured overnight at 37° C. in 10 ml Brain-heart Infusion (BHI) medium and subcultured for 2 hours and further diluted to obtain 104 CFU/ml. Eight week old female BALB/c mice (Harlan Lab) were used. Intranasal instillation of 102 CFU of *K. pneumoniae* in a volume of 10 µl was performed by holding the mice in an upright position under anesthesia. Following the infection, 20 µl of the following treatment was injected via the i.n. route (intra nasal): 20 µg of IL-26; 50 µg LL-37 (positive control) or PBS (negative control). Another control was intranasal infection of mice with IL-26 pre-treated bacteria (102 CFU+20 µg IL-26 mixed for 1 hour prior injection). Seventy-two hours post-challenge, mice were euthanized, and blood, lungs and spleens were collected. Lungs and spleens were weighted and homogenized with a Potter-Elvehj em Pestle. Diluted blood, lungs, and spleen homogenates in NaCl were cultured overnight on blood agar plates before bacterial colonies were counted by two independent investigators.

Isolation of Peripheral Blood Cells

Peripheral blood mononuclear cells (PBMCs) were obtained by Ficoll centrifugation of blood buffy coats. Monocytes, NK cells, and pDC were then isolated by magnetic separation using the following commercial available kits: Monocyte Isolation kit II (Miltenyi), EasySep™ Human NK cell Enrichment kit (StemCell), and Diamond pDC Isolation kit II (Miltenyi). Macrophages were differentiated by culturing monocytes with 50 ng/nl GM-CSF for 5 days. After Ficoll centrifugation, the high density granulocytes fraction was used to isolate Neutrophils using CD15 Microbeads (Miltenyi). Purity was routinely >95%, assessed by flow cytometry of: CD14+ monocytes, CD56+ NK cells, BDCA2+ CD123+ pDC, CD14+ CD68+ FSChigh Macrophages, and CD15+ SSChigh Neutrophils.

Microarray Analysis

Total RNA from sorted cells was immediately isolated with the RNeasy kit from QIAGEN, and used to generate cDNA according to the Expression Analysis Technical Manual (Affymetrix). cRNA samples were generated with the Bioarray High-Yield RNA Transcript Labeling kit (ENZO) and Human Genome U133 plus 2.0 array according to the manufacturer's protocol (Affymetrix). The scanned images were aligned and analyzed using the GeneChip software Microarray Suite 5.0 (Affymetrix) according to the manufacturer's instructions. The signal intensities were normalized to the mean intensity of all the genes represented on the array, and global scaling (scaling to all probe sets) was applied before performing comparison analysis. Genes with variable expression levels were selected based on the following criteria: genes should be expressed (have presence calls) in at least one of the three samples and σi/µi ratio should be >0.65, where σi and µi are the standard deviation and mean of the hybridization intensity values of each particular gene across all samples, respectively.

In Vitro Generation and Characterization of IL-26-DNA Complexes

IL-26-DNA complexes were generated by mixing 600 ng of bactDNA (Life Technologies) or huDNA (BioChain) with different concentration of recombinant IL-26 in 40 µl of nuclease-free water (Ambion) and then diluted into 200 µl of complete medium for cell stimulation (final concentrations: 3 µg/ml DNA and 0.1 up to 1 µM IL-26). IL-26-DNA complexes were visualized by 1.5% agarose gel migration or by confocal microscopy after staining DNA with DAPI (0.1 ng/ml; Sigma-Aldrich) or by using Alexa488-labeled DNA. DNA labeling with Alexa 488 was performed using the Ulysis Nucleic Acid Labeling Kit (Molecular Probes), that uses a platinum dye complex to form a stable adduct with the N7 position of a guanine as well as with less efficiency to adenine bases in DNA. To detect IL-26, suspensions containing precipitating complexes were stained overnight with a mouse anti-IL-26 antibody (Clone 142-69-1), followed by careful washes and incubation with Alexa 546-labeled anti-mouse secondary antibody for 1 h.

Generation of TH17 Cells and TH17 Clones

CD4 naive T cells were enriched from buffy coats of healthy volunteers with the CD4+ Naïve T Cell Isolation Kit II (Miltenyi Biotec). Afterwards, the cells were sorted on a FACSAria (Becton Dickinson) as CD45RA+, CD4+, CD8−, CD14−, CD16−, CD20−, CD56−, γδTCR−, BDCA2−, CD11c−, CD25−, CD45RO− to reach a purity of >95% of naïve CD4+CD45RA+ T cells. These cells were then plated in flat bottom plates at 5×104 cells/well and cultured for 5 days in the presence of plate-bound anti-CD3 (10 µg ml-1) and soluble anti-CD28 (1 µg ml-1) plus IL-1β (10 ng/ml)+IL-6 (20 ng/ml)+TGF-β (1 ng/ml)+TNF-α (10 ng/ml)+IL-23 (100 ng/ml) in Yssel's Medium (Gemini)23. As a control, naïve T cells were also stimulated (i) without cytokines, (ii) IL-12 (5 ng/ml)+IFN-γ (20 ng/ml)+anti-IL-4 (10 µg/ml) and (iii) IL-4 (25 ng/ml)+anti-IFN-γ (10 µg/ml) to generate Th0, Th1, and Th2 cells respectively. All cytokines used for polarization were purchased from R&D Systems. For the TH17 clones, 1G3, 7H1 and 72G6 cells were generated as described previously and cultured in RPMI 1640 (Invitrogen) supplemented with 2 mmol/L L-glutamine, 0.05 mmol/L β-mercaptoethanol, 10% human male AB serum (GemCell), 300 IU/mL IL-2, 5 ng/mL IL-1β and 10 ng/mL IL-23 in the presence of the irradiated feeder EBV B-cell line LCL111 at 0.3*106/mL To generate supernatants, primary TH17 cells or TH17 clones were restimulated with anti-CD3/anti-CD28 in antibiotic-free medium and cell-free supernatants were harvested 24 hours later. IL-26 protein levels in TH17 cells supernatants were measured by ELISA (USCN Life Science). In some experiments, TH17 clones were transfected with 80 pmols of control siRNA-A (scrambled sequence) or siRNA targeting IL-26 complexed with 6 μl of siRNA Transfection reagent according to the manufacturer's protocol (Santa Cruz Biotechnology) for 6 hours at 37° C. Cells were then washed and restimulated with anti-CD3/anti-CD28 in antibiotic-free medium and cell-free supernatants were harvested 24 hours later. IL-26 concentration in the different supernatants was measured by ELISA (Cusabio Biotech).

Real-Time PCR Analysis

Polarized TH0, TH1, TH2, and TH17 cells were harvested, lyzed with the TRI Reagent (Ambion), and stored at −20° C. Total RNA was extracted using the RiboPure kit (Ambion) and cleaned with the RNAqueous kit (Ambion). One μg of RNA was then reverse transcribed into cDNA (High Capacity cDNA, Applied Biosystems). For each individual gene, 20 ng of cDNA was amplified for expression analysis using Taqman on an ABI 7500 Fast system. Human GAPDH mRNA levels were quantified and used for normalization as previously described30. Human Taqman probes used were: IL26 (Hs00218189_m1), IL17A (Hs00174383_m1), IL17F (Hs00369400_m1), IL22 (Hs01574154_m1), IFNG (Hs00989291_m1), IL13 (Hs00174379_m1) and were all purchased at Life Technologies.

Imaging of IL-26-DNA Complexes in TH17 Supernatants

DNA-IL-26 complexes in TH17 cell supernatants were visualized by staining precipitating complexes with 10 μg/ml mouse anti-IL-26 antibody (clone 142-69-1) for 2 h, followed by incubation with Alexa 546-labeled anti-mouse secondary antibody for 1 h. After further washes DAPI (0.1 ng/ml) was added to stain DNA and visualized by confocal microscopy.

Stimulation of Immune Cells by IL-26-DNA Complexes or TH17 Supernatants

Purified immune cells were cultured in 96-well round-bottom plates at 5×104/well in 200 μl RPMI 1640 (GIBCO) supplemented with 10% FCS (Atlanta biologicals) and Pen/Strep in the presence of 1 μM IL-26, bactDNA or huDNA, or IL-26-DNA complexes. Viability of cells after culture was assessed by flow cytometry using 7-AAD staining according to the manufacturer's protocol (BioLegend). In some experiments, pDC were stimulated with different amounts of live bacteria (P. aerug), different concentrations of DNA content from chemically-lyzed bacteria (50 mM Tris pH 8.0, 0.1% Triton X-100) or different amounts of 1.106 cell/ml live or UV-treated dying 293T cells in the presence of 10 μM IL-26. PDC were also stimulated with various amounts of supernatants derived from TH0 or TH17 cells alone or supplemented with 3 μg/ml huDNA. In some experiments the supernatants or in vitro generated complexes were pretreated with DNase I (1,000 U/ml) or heparin (up to 10 U/ml). The different immune cell supernatants were collected after overnight culture and the levels of cytokine production were measured by ELISA: IL-1β, IL-6, TNF-α (R&D systems) and IFN-α (PBL Biomedical Laboratories).

Uptake and Internalization of IL-26-DNA Complexes by pDC

Purified pDC were incubated with 3 μg/ml Alexa488-labeled DNA mixed with 1 μM IL-26 at 5×104/well in 200 μl RPMI 1640 (GIBCO) supplemented with 10% FCS (Atlanta biologicals) for 3 hours at 37° C. Cells were then fixed with 4% paraformaldehyde and stained for the pDC specific marker CD123 (anti-CD123-APC, BD Biosciences) and analyzed by flow cytometry (FACS Calibur, BD). Alternatively, cells were let attach to poly-L-lysine coated coverslips for 3 hours, fixed with 4% paraformaldehyde and stained for the pDC specific marker CD123 (anti-CD123-PE, clone 7G3, BD Biosciences) or the early endosome marker CD71 (anti-CD71-biotin, clone M-A712, BD Biosciences+streptavidin-PE), and mounted in ProLong®+DAPI (Life Technologies).

TLR9 Reporter Gene Assay

Human embryonic kidney (HEK) cells 293 that stably co-express a human TLR4 or TLR9 gene and an NE-κB-inducible SEAP (secreted embryonic alkaline phosphatase) reporter gene were purchased from Invivogen. After TLR4 or TLR9 activation, secreted SEAP levels were detected in the cell-free supernatant using QUANTI-Blue medium (InvivoGen) and quantified by reading the OD at 620 nm.

Tissue Homogenization for IL-26 ELISA

The skin biopsies were transferred into polypropylene tubes containing 1 ml buffer consisting of PBS supplemented with 1M NaCl and protease inhibitor (Protease Inhibitor Cocktail Set III; Merck Millipore) before the homogenization was performed using a Polytron PT 2500 E (Kinematica, Switzerland). The homogenates were then transferred into Protein Low Bind Tubes (Eppendorf) and centrifuged at 5000×g for 5 min at 4° C. The resulting supernatant was stored at −20° C. In order to determine the concentration of total protein the Pierce® BCA Protein Assay Kit (Thermo Scientific) was used according the manufacturer's protocol. The samples' total protein concentration was subsequently adjusted to 100 μg/ml prior measuring IL-26 concentration by ELISA (Cusabio Biotech). The concentration of IL-26 in the original skin-biopsy sample was then estimated by dividing the total amount of IL-26 measured in each sample by the skin-biopsy volume. The skin-biopsy volume in a cylindrical 3-mm punch-biopsy specimen was estimated to be: $h \times (\pi \times r^2) = 3 \times (\pi \times 1.52) = 21.2$ mm3=21.2 μl.

Statistical Analysis

Statistical analyses were performed with the two-tailed unpaired Student t-test for in vitro experiments and with the unpaired non parametric Mann-Whitney U test for in vivo experiments and patients samples analyses. $P<0.05$ was considered significant. Group sizes, reproducibility and p values for each experiment are given in the corresponding figure legend.

Example 1: IL-26 is a Cationic and Amphipathic Multimeric Protein

The sequence analysis of IL-26 revealed an unusual cationicity of this cytokine: calculated charge of +18.1 at pH 7 and isoelectric point of 10.4.

The majority of the cationic charges were found to be contained within, or adjacent to, 2 out of the 6 predicted helices of the protein: helices B and E contain three arginines and seven lysines. Three-dimensional modelling of the protein revealed a close proximity of helices B and E, leading to cluster formation and surface exposure of the cationic residues. On the opposite side of this cluster, resides a hydrophobic patch (helix A) composed of several hydrophobic side chains (alanine 23, isoleucine 26, alanine 29, tryptophan 30, alanine 33). The predominance of polar (cationic) residues on one side of the molecule and hydrophobic amino acids on the opposite side indicated that IL-26 is a cationic amphipathic protein.

The structure of IL-26, was further analyzed by small angle X-ray scattering (SAXS) analysis of recombinant human IL-26 (rhIL-26). IL-26 did not only form dimers, but was also able to form higher-degree multimers. This represents an atypical structure when compared to close homologues IL-10 and IL-22, which can only dimerize. Interestingly, IL-26 multimers were found to adopt a beads-on-string shape, giving rise to elongated structures. Thus, IL-26 is a highly cationic and amphipathic protein that forms elongated multimers, representing a highly atypical structure compared to other cytokine such as IL-10 and IL-22 of the same family.

Example 2: Mouse Monoclonal Antibodies

The mouse antibody has been raised against an antigenic construct comprising an antigenic peptide corresponding to the amino acid sequence of recombinant human IL-26 rhIL-26 from R&D systems. For eliciting and preparing antibodies, 6-8 weeks old BALB/c mice are immunized with the antigenic recombinant human IL-26 peptide. Immunogenicity of the antigenic construct is determined by probing sera samples in suitable time intervals after immunization using an immunoassay such as, for example, an ELISA assay. The immunogen can be administered alone, or mixed with adjuvant, or expressed from a vector (VEE replicon vector, vaccinia), or as DNA, or as a fusion protein to induce an immune response.

After the animal is boosted, for example, two or more times, spleen cells are harvested from the immunized animals and hybridomas generated by fusing sensitized spleen cells with a myeloma cell line, such as murine SP2/O myeloma cells (ATCC, Manassas, Va.) using the well-known processes of Kohler and Milstein (Nature 256: 495-497 (1975)) and Harlow and Lane (Antibodies: A Laboratory Manual (Cold Spring Harbor Laboratory, New York 1988)).

The antigenic construct according to the invention, particularly a vaccine composition comprising said antigenic construct in a pharmaceutically acceptable form, is administered in repeated doses, in particular in 1 to 15 doses, more particularly in 2 to 10 doses, even more particularly in 3 to 7 doses but especially in 4 to 6 doses, in time intervals of between 1 and 10 weeks, particularly in time intervals of between 1 and 6 weeks, more particularly in time intervals of between 1 and 4 weeks, and even more particularly in time intervals of between 2 and 3 weeks. The immune response is monitored by taking Sera samples at a suitable time after boosting, particularly 3 to 10 days after boosting, more particularly 4 to 8 days after boosting and more particularly 5 to 6 days after boosting and determining the immunogenicity of the antigenic construct using known methodology, particularly one of the commonly used immunoassays such as, for example, an ELISA assay Immunization with the antigenic construct according to the invention, but particularly with a vaccine composition comprising the antigenic construct according to the invention in a pharmaceutically acceptable form leads to a significant immune response in the treated animal. Animals, but especially mice with therapeutic titers are selected for a fusion of antibody producing cells, particularly B-lymphocytes with a continuously growing or immortal cell line, such as a myeloma cell line. The cells are induced to fuse by the addition of polyethylene glycol. Therapeutic titers are those which give a positive result in an ELISA assay in a dilution of between 1:4000 and 1:6000, particularly of between 1:4500 and 1:5500, more particularly of 1:5000.

The resulting hybrid cells are then cloned in the conventional manner, e.g. using limiting dilution, and the resulting clones, which produce the desired monoclonal antibodies, cultured.

The so obtained hybridomas are chemically selected by plating the cells in a selection medium containing hypoxanthine, aminopterin and thymidine (HAT).

Hybridomas are subsequently screened for the ability to produce monoclonal antibodies against IL-26. Hybridomas producing antibodies of interest are cloned, expanded and stored frozen for future production. The preferred hybridoma produces a monoclonal antibody such as clone 142-84-B1 having the IgG isotype, more preferably the IgG1 isotype.

Example 3: Sequence Listing of the Isolated and Purified Mouse Monoclonal Antibody Clone 142-84-B1 that Recognizes and Binds IL-26 as Well as Chimeric and Humanized Antibodies Thereof

```
Sequences of the monoclonal antibody clone 142-84-B1.
```

Heavy Chain (HC)
84 HC DNA: corresponding to SEQ ID No 1
CAGGTTCAACTGCAGCAGTCTGGGGCTGAGCTGGTGAGGCCTGGGGCTTCAGTGAC
GCTGTCCTGCAAGGCCTCGGGCTT
CACATTTCCTGACTATGAAATACACTGGGTGAGGCAGACACCTGTGCATGGCCTGGA
ATGGATTGGAGGTATTGATCCTG
AAACTGGTGATACTGCCAACAATCAGAAGTTCAAGGGCAAGGCCACACTGACTGCA
GACACATCCTCCAGCACAGCCTAC
ATGGAGCTCCGCAGCCTGACATCTGAGGACTCAGCCGTCTATTACTGTACAAGATTC
TACGGTAGTTTTGACTACTGGGA
CCAAGGCACCACTCTCACAGTCTCCTCA 84 HC AA: corresponding to SEQ ID No 3
QVQLQQSGAELVRPGASVTLSCKASGFTFPDYEIHWVRQTPVHGLEWIGGIDPETGDTA
NNQKFKGKATLTADTSSSTAY
MELRSLTSEDSAVYYCTRFYGSFDYWDQGTTLTVSS -continued Sequences of the monoclonal antibody clone 142-84-B1.

Light Chain (LC)
84 LC DNA: corresponding to SEQ ID No 2
AACATTATGATGACACAGTCGCCATCATCTCTGGCTGTGTCTGCAGGAGAAAAGGTC
ACTCTGAGCTGTAAGTCCAGTCA
AAGTGTTTTATACAGTTCAAATCAGAAAAATTACTTGGCCTGGTACCAGCAGAAACC
AGGGCAGTCTCCTAAACTACTGA
TCTACTGGGCATCCACTAGGGAATCTGGTGTCCCTGATCGCTTCACAGGCAGTGGAT
CTGGGACAGATTTTACTCTTACC
ATCAGCAGTGTACAAGCTGAAGACCTGGCAGTTTATTACTGTCATCAATACCTCTCC
TCGTACACGTTCGGAGGGGGGAC
CAAGCTGGAAATAAAA 84 LC AA: corresponding to SEQ ID No 4
NIMMTQSPSSLAVSAGEKVTLSCKSSQSVLYSSNQKNYLAWYQQKPGQSPKLLIYWAST
RESGVPDRFTGSGSGTDFTLTISSVQAEDLAVYYCHQYLSSYTFGGGTKLEIK Determination of the CDRs:
Heavy Chain
QVQLQQSGAELVRPGASVTLSCKASGFTFPDYEIHWVRQTPVHGLEWIGGIDPETGDT
ANNQKFKGKATLTADTSSSTAYMELRSLTSEDSAVYYCTRFYGSFDYWDQGTTLTVSS CDR-H1: GFTFPDYEIH corresponding to SEQ ID No 5

CDR-H2: GIDPETGDTANNQKFKG corresponding to SEQ ID No 6

CDR-H3: FYGSFDY corresponding to SEQ ID No 7

Light Chain
NIMMTQSPSSLAVSAGEKVTLSCKSSQSVLYSSNQKNYLAWYQQKPGQSPKLLIYWAS
TRESGVPDRFTGSGSGTDFTLT1SSVQAEDLAVYYCHQYLSSYTFGGGTKLEIK CDR-L1: KSSQSVLYSSNQKNYLA corresponding to SEQ ID No 8

CDR-L2: WASTRES corresponding to SEQ ID No 9

CDR-L3: HQYLSSYT corresponding to SEQ ID No 10

In an aspect, a chimeric antibody or a fragment thereof, or a humanized antibody or a fragment thereof may be provided which comprises in the variable region at least one CDR of non-human origin embedded in one or more human- or primate-derived framework regions and combined with a constant region derived from a human or primate source antibody, which chimeric antibody or a fragment thereof, or a humanized antibody or a fragment thereof is capable of specifically recognizing and binding IL-26 peptide.

In another aspect, a humanized antibody or fragment thereof may be provided, in which the C-terminal Lys of the heavy chain constant region has been removed.

In a further aspect, a humanized antibody or fragment thereof may be provided, which humanized antibody or fragment thereof is of the IgG1, IgG2, IgG3, or IgG4 isotype.

Example 4: Blocking IL-26 with the Anti-IL26 Ab for the Treatment of Psoriasis

Psoriasis is a common T-cell-mediated inflammatory disease of the skin, which, in its most prevalent form, is characterized by the appearance of scaly erythematous plaques that may cover large areas of the patient's body. A key feature of psoriasis is the abnormal activation of dendritic cell (DC) subsets in the dermal compartment leading to the downstream T-cell-mediated autoimmune cascade. A role for plasmacytoid DCs (pDCs) producing type I IFNs appears to be central in this process. pDC-derived IFNs activate conventional DCs that stimulate autoimmune T cells to migrate into the epidermis. Here, these T cells produce Th17 cytokines IL-17 and IL-22 [6, 7], which directly initiate keratinocyte proliferation and an abnormal epidermal differentiation pattern.

Applicants found that IL-26 has the ability to break innate tolerance to extracellular DNA and trigger activation of pDC together with the finding that IL-26 is overexpressed in psoriatic skin at concentrations that are relevant for pDC activation, suggest that IL-26 could represent a key trigger of pDC activation and of psoriasis development. To test this approach Applicants repeatedly injected IL-26 into murine skin. Of note in the mouse system there is no IL-26R and therefore any potential effect of IL-26 may by driven by receptor—independent effects that Applicants had described.

Figure 7:
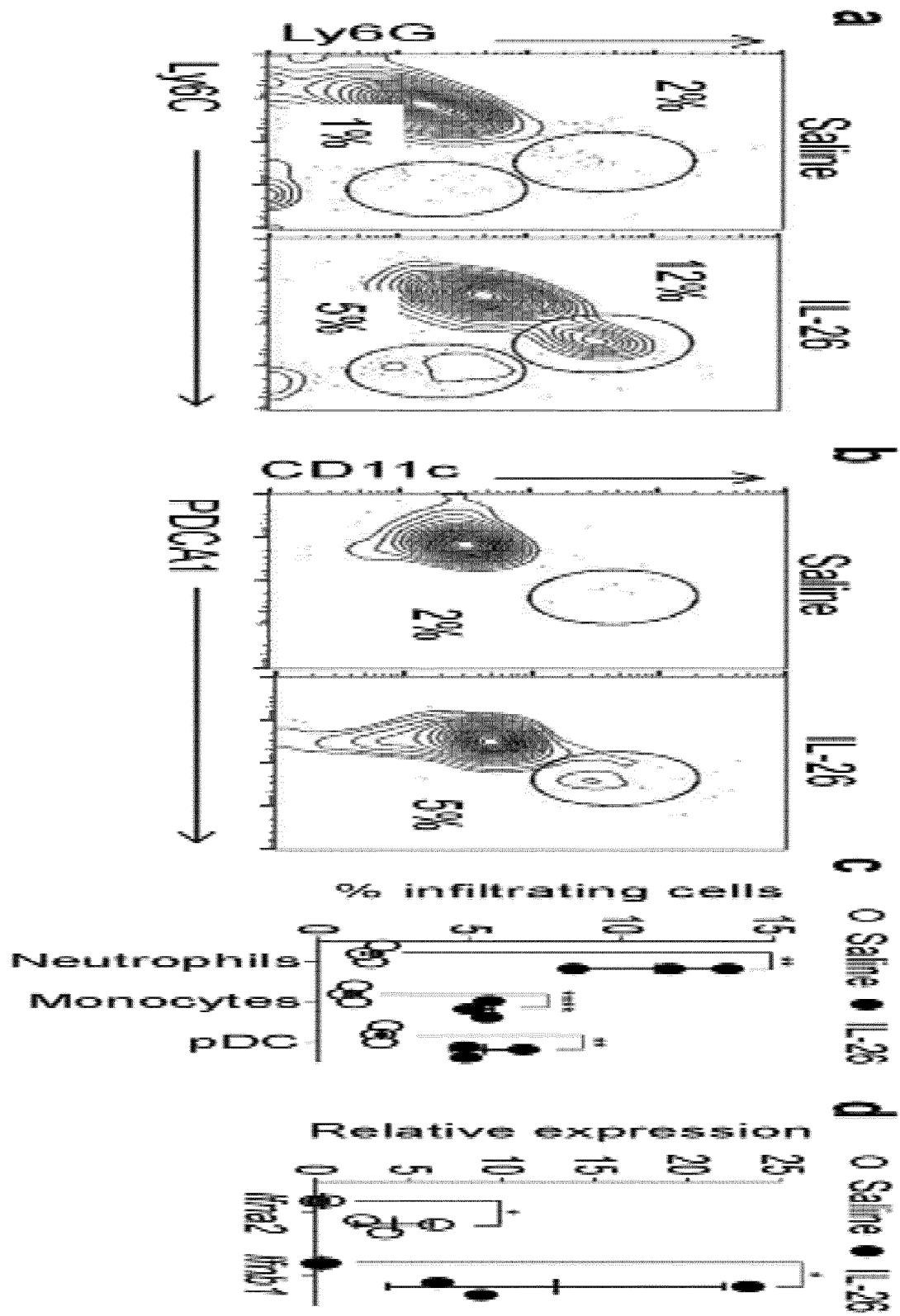
FIG. 7. Intradermal injection of IL-26 leads to immune cell infiltration and type I IFN production. Neutrophils, monocytes (a) and pDC (b) infiltration in mouse skin intradermally injected with either Saline or 1 μg of IL-26. Data are representative of three mice per group. (c), Percentages of infiltrating neutrophils (Ly6Ghigh Ly6Cint CD11b+), monocytes (Ly6Cint Ly6Chigh CD11b+) and pDC (B220+ CD11c+ PDCA1+) in dermal single cell suspensions isolated from injected skin was measured by flow cytometry. Data are the mean±SD of three mice per group *p<0.001, p<0.01, *p<0.05 unpaired student's t test. (d), Relative ifna2 and ifnb1 mRNA tissue expression of skin collected 24 hours after Saline or IL-26 injection. Data are the mean±SD of three mice per group. *p<0.05, unpaired student's t test.
Figure 8:
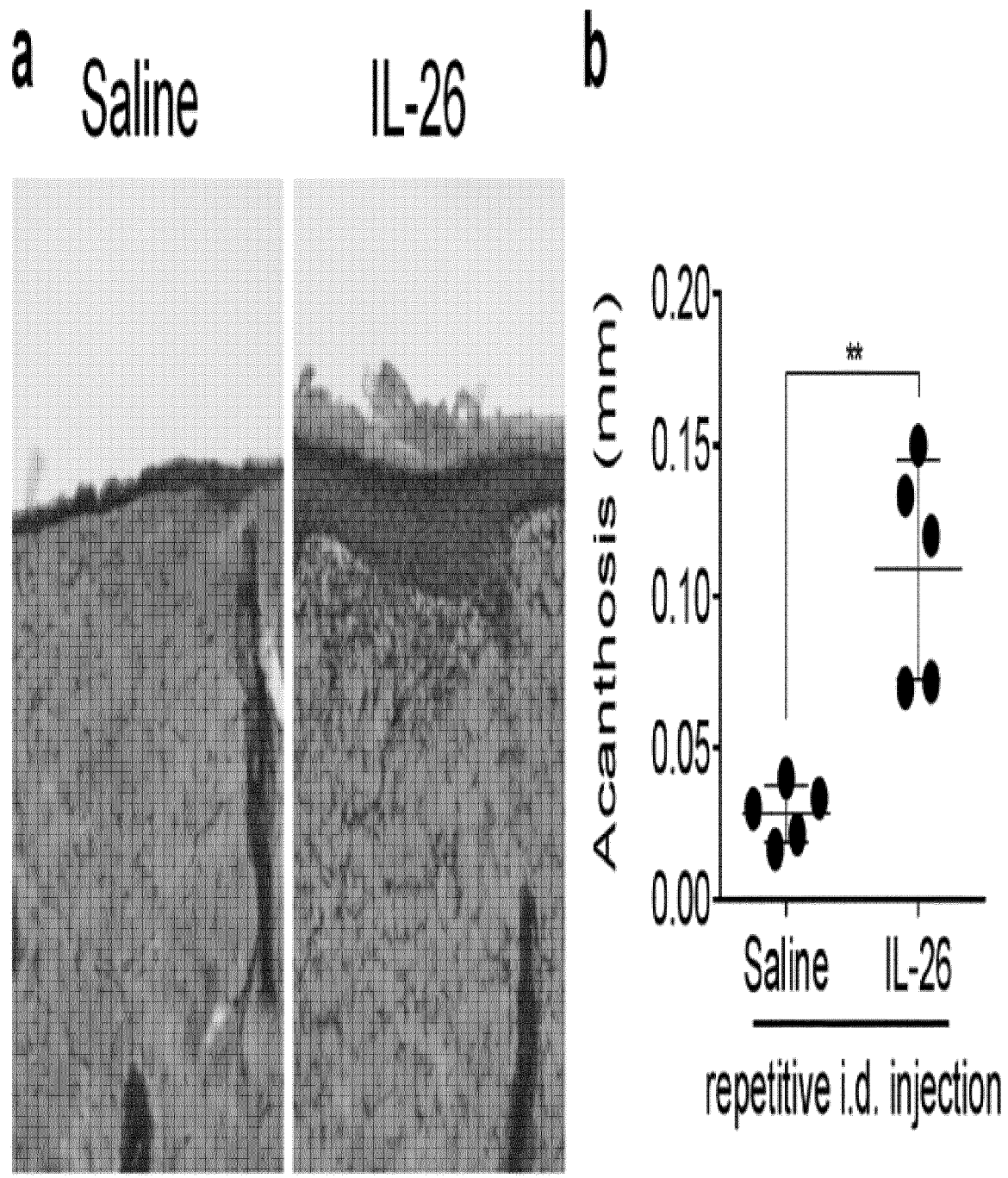
FIG. 8. Repetitive intradermal injection of IL-26 leads to psoriasiform skin inflammation in mice. (a) Representative HE staining of mouse skin injected every day with saline or with 1 μg of IL-26 for 5 days. (b) Quantification of acanthosis (epidermal thickness) of mouse skin treated as in (a). Data were obtained with 5 mice per group. **p<0.01, unpaired student's t test.

A single intradermal injection of IL-26 induced the recruitment and activation of pDC (FIG. 7), suggesting that this model is valid to test its inflammatory function. Applicants also found that repetitive intradermal injection of IL-26 over 5 days induced a sustained inflammation of the skin and epidermal acanthosis (FIG. 8) providing the evidence that IL-26 can induce a psoriasiform skin lesion.

The aim of this study consists in the generation of anti-IL26 antibodies and identifying clones that are able to inhibit the ability of IL-26 to activate pDC in vitro and in vivo, and to inhibit the IL-26 mediated induction of psoriasis.

Briefly, a BALB/c mouse less than 6 months of age was immunized with purified IL26 protein. Hybridomas secreting monoclonal antibodies recognizing IL26 were identified by ELISA. Three IL-26 specific clones were identified with high affinity for IL-26: clone 69 (IgG1), clone 73 (IgG1), and clone 84 (IgG1).

Figure 9:
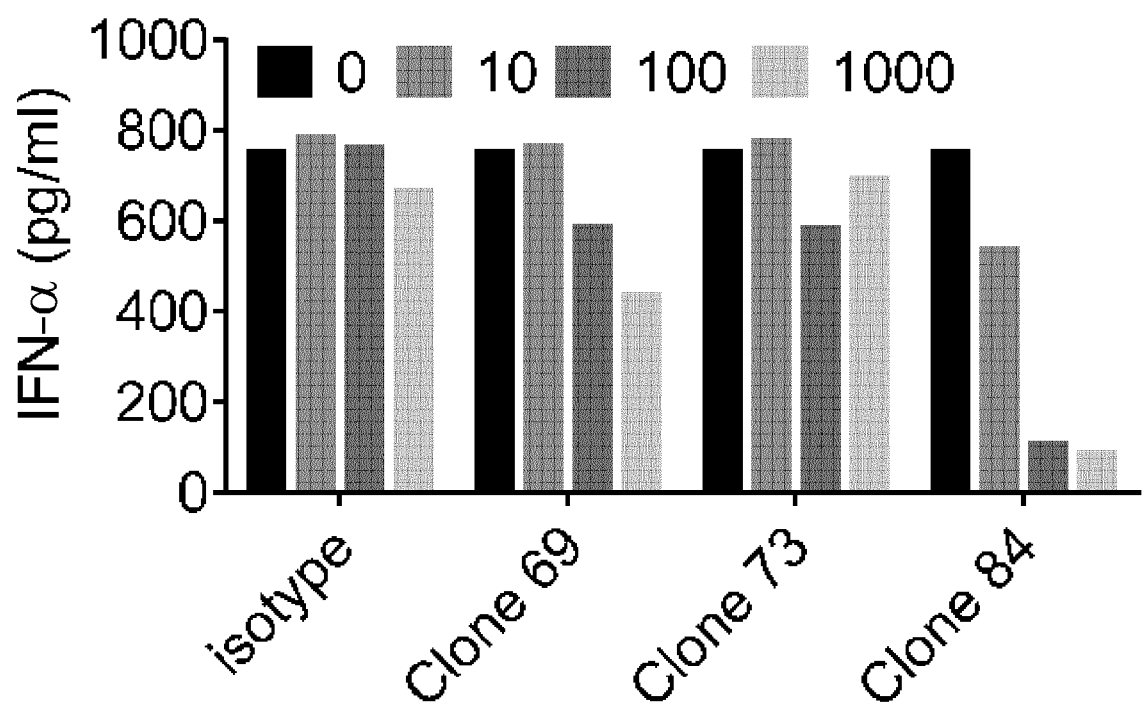
FIG. 9. The anti-IL-26 antibody clone 84 inhibits IFN production induced by IL-26-DNA complexes. IFN-α produced by pDC stimulated overnight with IL-26 (1 μM)+DNA (3 μg/ml) with or without 10, 100, and 1000 μg/ml of the anti-IL-26 antibody clones 69, 73, or 84 (142-84-B1), or isotype control.

Applicants then tested the clones for their ability to block the immunogenicity of IL-26-DNA complexes in-vitro. Briefly, Applicants generated IL-26—DNA complexes by mixing 600 ng of human DNA (BioChain) with recombinant IL-26 in 40 µl of nuclease-free water (Ambion) and then diluted them into 200 µl of complete medium for pDC stimulation (final concentrations: 3 µg/ml DNA and 1 µM IL-26). Increasing concentrations of clone 69, clone 73 and clone 84 (10 µg/ml, v) were added into the final cultures. IFN-α was measured in the supernatants of pDC after overnight culture. Clone 84 (namely 142-84-B1), but not clones 69 or 73 efficiently inhibited IFN-α production by pDC at concentrations of 100 µg/ml, 1000 µg/ml (FIG. 9).

Figure 10:
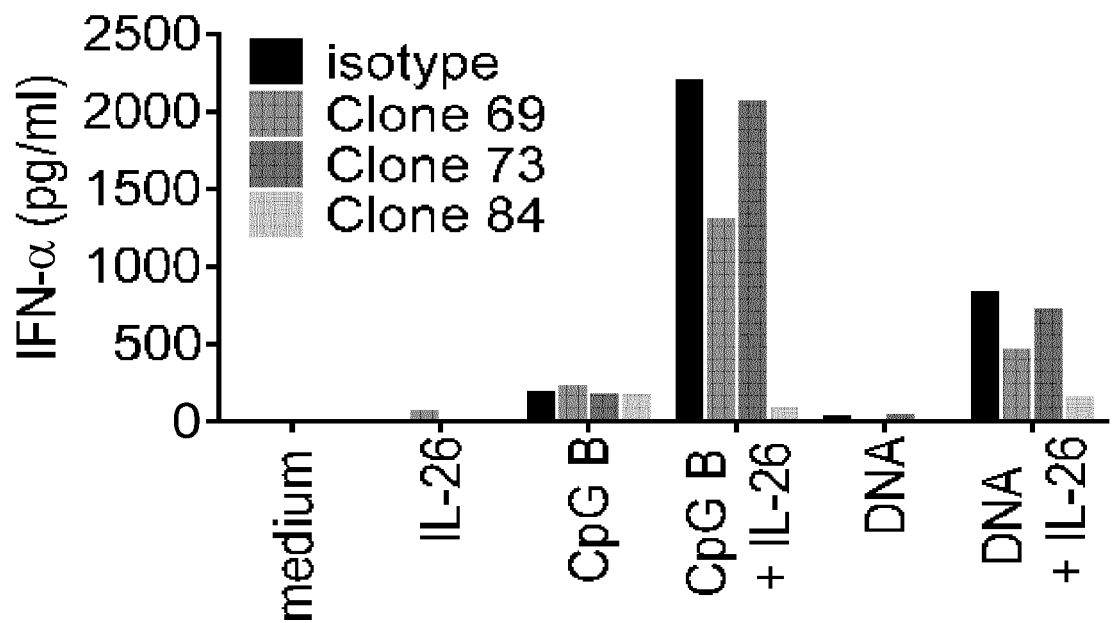
FIG. 10. The anti-IL-26 antibody clone 84 inhibits the ability of IL-26 to promote the immunogenicity of CpG-DNA and human DNA. IFN-α produced by pDC stimulated overnight with IL-26 (1 μM)+CpG (1 μM) or DNA (3 μg/ml) with or without 100 μg/ml of the anti-IL-26 antibody clones 69, 73, or 84, or isotype control.

This findings were further confirmed by using phosphodiesteric CpG oligonucleotides, which are a potent inducer of IFN when complexed with IL-26 but not when given alone (FIG. 10). Again only clone 84 but not clones 69 or 73 was able to block the ability of IL-26 to promote the immunogenicity of CpG-DNA (FIG. 10).

Figure 11:
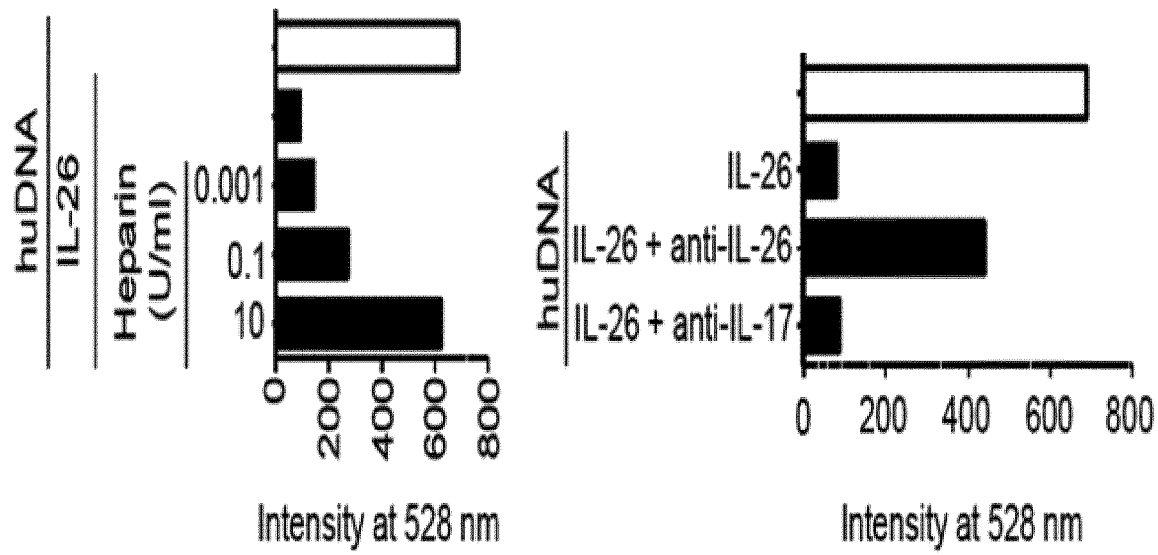
FIG. 11. The anti-IL-26 antibody clone 84 inhibits complex formation of IL-26 with DNA. Fluorimetric quantification of DNA staining by the picogreen dye upon mixing of huDNA with IL-26 in the presence of (left panel) increasing concentrations of the anionic polymer heparin, or (right panel) neutralizing anti-IL-26 (clone 142-84-B1) or anti-IL-17 antibodies.

The ability of clone 84 to neutralize IL-26 binding to DNA was shown in the picogreen staining experiment. FIG. 11 shows that the inability of the Picogreen dye to stain DNA because of its binding to IL-26 is restored by the anti-IL-26 antibody clone 84 (FIG. 11), indicating that it inhibits binding of IL-26 to DNA.

Figure 12:
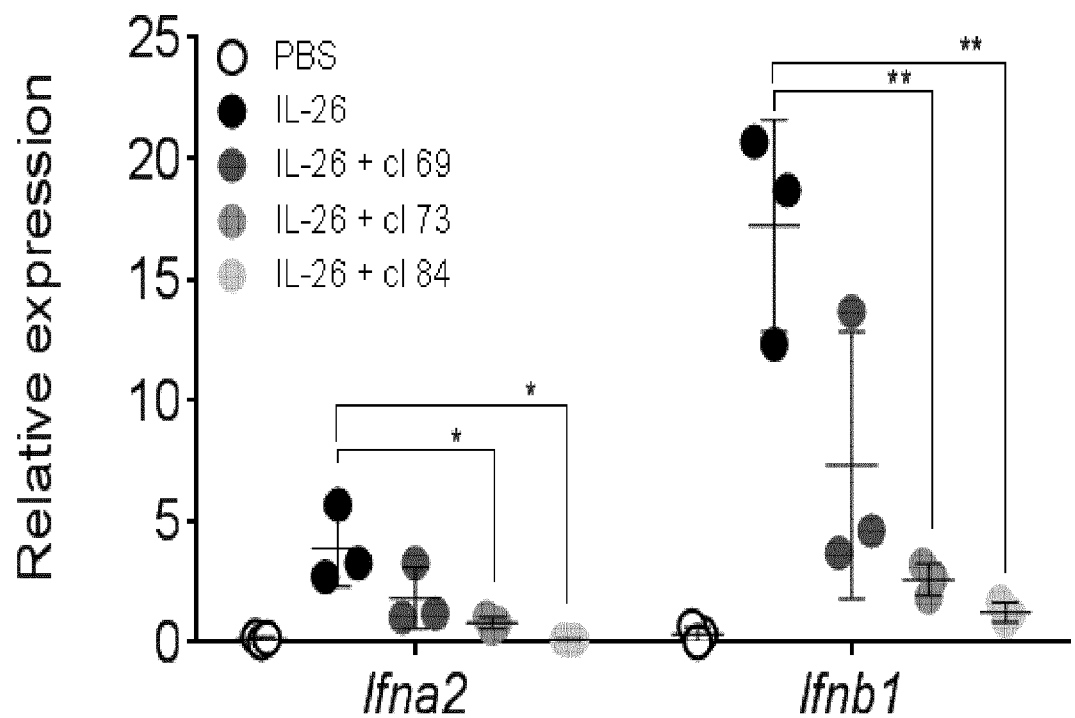
FIG. 12. The anti-IL-26 antibody clone 84 inhibits type I IFN expression induced by intradermal IL-26 injection. Relative ifna2 and ifnb1 mRNA tissue expression of skin collected 5 days after Saline or IL-26 daily injection with or without the anti-IL-26 antibody clones 69, 73, or 84. Data are the mean±SD of three mice per group.
Figure 13:
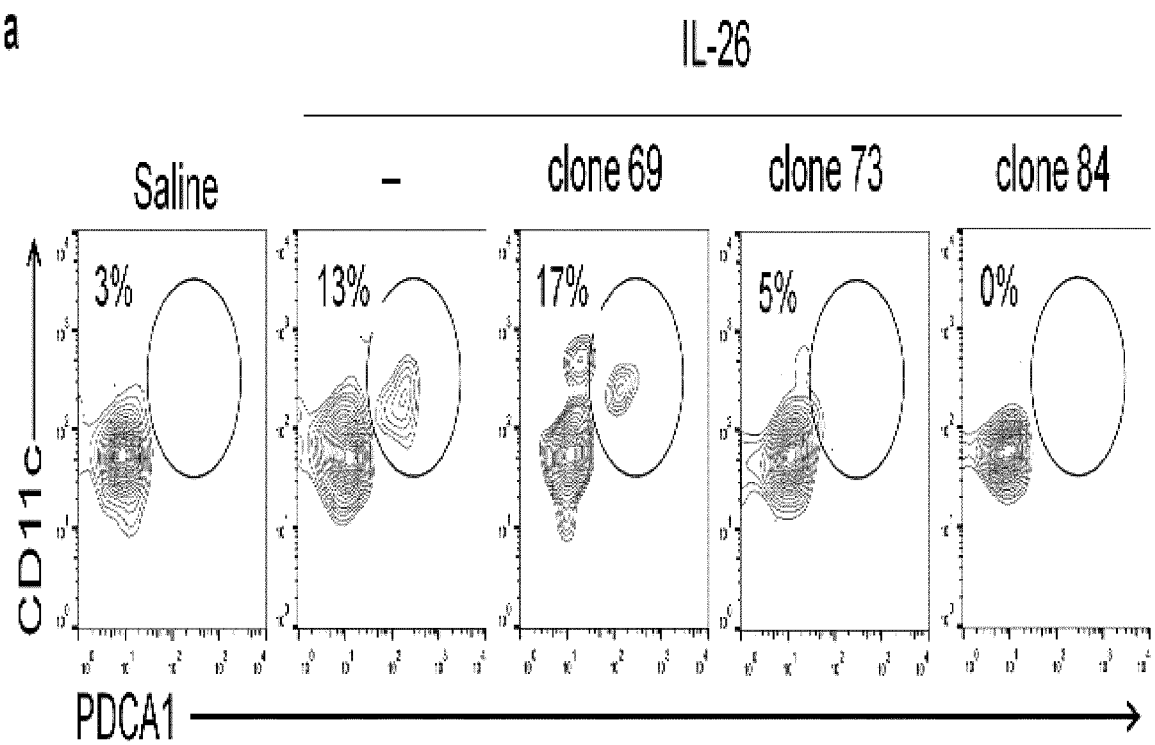
FIG. 13. The anti-IL-26 antibody clone 84 inhibits skin infiltration of pDC induced by intradermal IL-26 injection. (a) pDC infiltration in mouse skin intradermally injected everyday for 5 days with either Saline or 1 μg of IL-26 with or without 10 μg of the anti-IL-26 antibody clones 69, 73, or 84. Data are representative of three mice per group. (b) Percentages of infiltrating pDC (CD45+ B220+ CD11c+ PDCA1+) in dermal single cell suspensions isolated from injected skin was measured by flow cytometry. Data are the mean±SD of three mice per group **p<0.0001, *p<0.001, unpaired student's t test. (c) Quantification of acanthosis (epidermal thickness) of mouse skin treated as in (a). Data were obtained with 3 mice per group. *p<0.05, unpaired student's t test.
Figure 13:
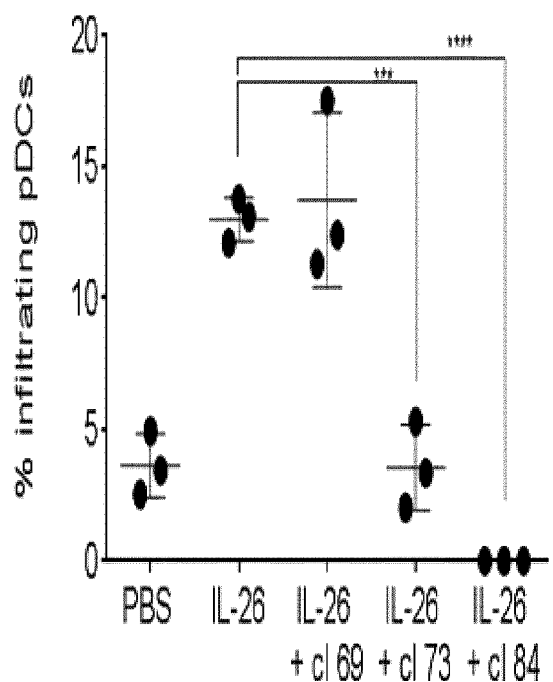
Figure 13:
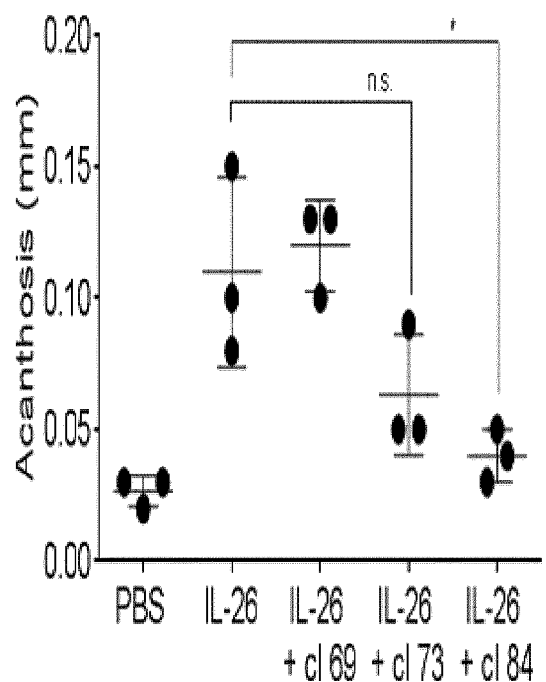

To determine whether anti-IL-26 antibodies would block IFN production by pDC in-vivo Applicants took advantage of the cutaneous IL-26 injection model. As described above, repetitive IL-26 injection yielded strong pDC infiltration and type I IFN production. Applicants have previously shown that skin infiltration of pDC is largely dependent on their type I IFN production, in a self-amplifying loop. Intradermal injection of 10 µg of the anti-IL-26 antibody clone 84 every day for 5 days led to a complete inhibition of type I IFN expression and pDC infiltration (FIGS. 12 and 13a-b). By contrast, treatment with clone 69 and clone 73 only showed partial effects, confirming the in-vitro data (FIGS. 12 and 13a-b).

Thus the anti-IL-26 antibody clone 84 blocks the induction of type I IFNs and pDC infiltration in IL-26 injected skin. Type I IFN expression by pDC in the skin is a key event that initiates inflammation and the induction of the epidermal psoriatic phenotype. Indeed Clone 84 significantly inhibited T cell infiltration (not shown) and the development of the psoriatic phenotype (FIG. 13c).

Example 5: Recombinant IL-26 Kills Extracellular Bacteria by Pore Formation

Figure 1B:
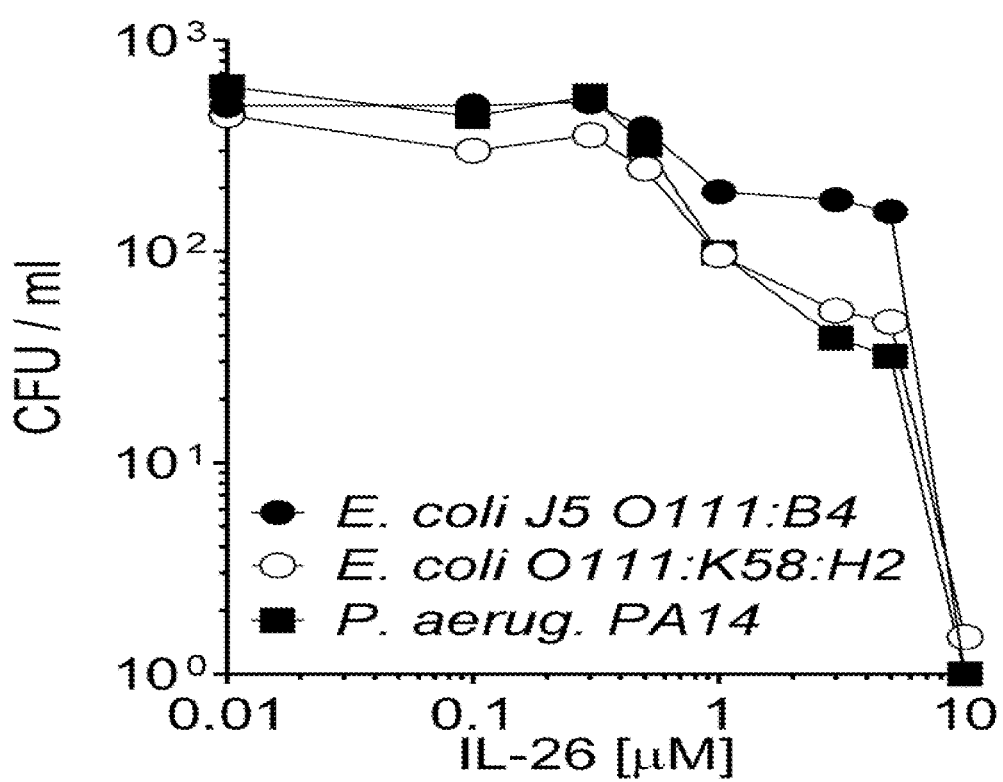
FIG. 1(b). Antimicrobial activity of rhIL-26 (a), Growth of the virulent strains *E. coli* J5 O111:B4, *E. coli* O111:K58:H2, and *Pseudomonas aeruginosa* (*P. aerug.*) PA14 in culture with increasing concentrations of rhIL-26. Data are representative of 3 independent experiments.

Using microbroth dilution assays (MBDA), 5-10 microM rhIL-26 inhibited the growth of several gram-negative bacterial strains, including *Pseudomonas aeruginosa* (PA14), *Escherichia coli* (O1:K1:H7, O18:K1:H7, O111:B4, O111: K58:H2), *Klebsiella pneumonia* (O1:K2) (FIG. 1a and FIG. 1b). No inhibition of colony formation was observed with *Enterococcus faecalis* or *Candida albicans* at IL-26 concentrations up to 50 µM (Table 1).

TABLE 1

Minimal inhibitory concentration (MIC) determination of the IL-26 antimicrobial activity against several microorganisms. MIC of IL26 against *P. aeruginosa*, *E. coli*, *S. aureus*, *E. faecalis* and *C. albicans* determined by Microbroth dilution assays.

| Organism | MIC50 of IL-26 (µM) |
| --- | --- |
| *Pseudomonas aeruginosa* (ATCC27853) | 8.6 |

TABLE 1-continued

Minimal inhibitory concentration (MIC) determination of the IL-26 antimicrobial activity against several microorganisms. MIC of IL26 against *P. aeruginosa*, *E. coli*, *S. aureus*, *E. faecalis* and *C. albicans* determined by Microbroth dilution assays.

Figure 1C:
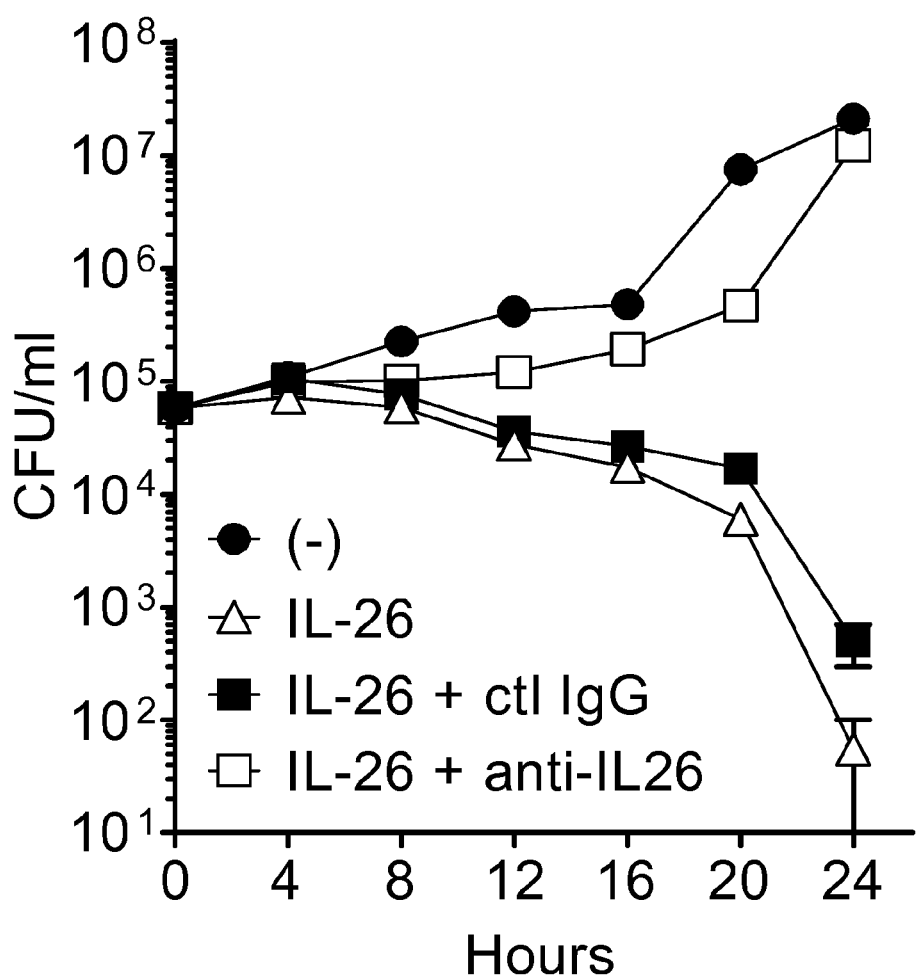
FIG. 1(c), Kinetics of *P. aerug.* growth cultured with or without 10 μM rhIL-26, in the presence of blocking anti-IL-26 or isotype control antibodies (ctl IgG).

| Organism | MIC50 of IL-26 (µM) |
| --- | --- |
| *Escherichia coli* (ATCC11775) | 18.6 |
| *Staphylococcus aureus* (ATCC6538) | 8.8 |
| *Enterococcus faecalis* (ATCC29212) | >50 |
| *Candida albicans* (ATCC24433) | >50 | rhIL-26, but not rhIL-17 or rhIL-22, efficiently inhibited *Pseudomonas aeruginosa* colony formation at concentrations of 10 µM. The observed inhibition of colony formation was due to bacterial killing as the number of colonies decreased over time (>log 2 over 24 h) (FIG. 1c). A loss of membrane integrity was confirmed by the decrease in bacterial staining using a fluorescent membrane-potential indicator dye and increased bacterial staining with an otherwise impermeable DNA dye.

To determine whether IL-26, kills bacteria by pore formation and membrane disruption, the ultrastructure of IL-26-treated bacteria was analyzed using scanning electron microscopy. As early as 30 min after treatment with 10 µM IL-26, the formation of membrane blebs on the surface of the bacteria was observed. In some instances, the disruption of the blebs with leakage of the cytosol into the extracellular environment was observed. These data indicate that, IL-26 disrupts bacterial membranes via pore formation.

Figure 1D:
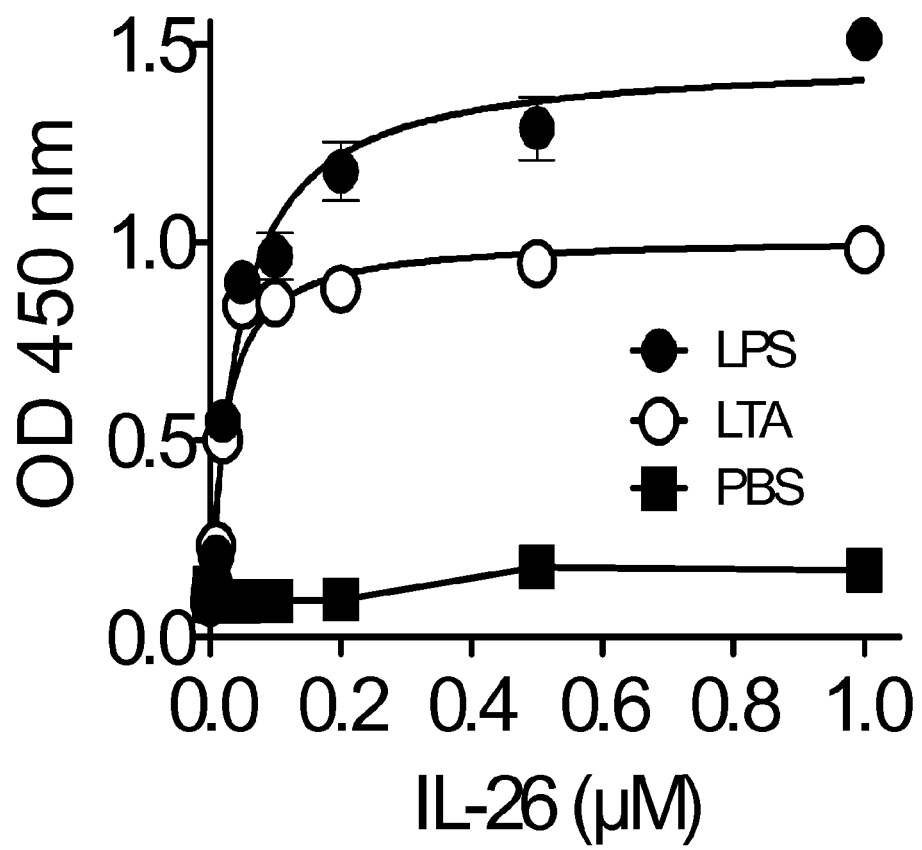
FIG. 1(d), IL-26 capacity to bind LPS or LTA assessed by an ELISA binding assay. Data are representative of 2 independent experiments, error bars represent the standard deviation of triplicate wells.

Furthermore, IL-26 has the ability to bind lipopolysaccharide (LPS) from gram-negative bacteria and lipoteichoic acid (LTA) from gram-positive bacteria (FIG. 1d and Table 2).

TABLE 2

IL-26 binds to the bacterial cell wall components LPS and LTA. Dissociation constants (KD) of IL-26, IL-22 or LL-37 binding to LPS or LTA, measured by ELISA. (NI) indicates no interaction.

| Protein | IL-26 | IL-26 | LL-37 | IL-22 | IL-22 |
| --- | --- | --- | --- | --- | --- |
| Ligand | LPS | LTA | LPS | LPS | LTA |
| KD (mean ± SD) | 40.5 nM ± 4.95 | 20.91 nM ± 2.84 | 3.45 nM ± 0.8 | NI | NI |

Example 6: The Mouse Model *K. pneumonia* Sepsis and Antimicrobial Activity of rhIL-26

Figure 1E:
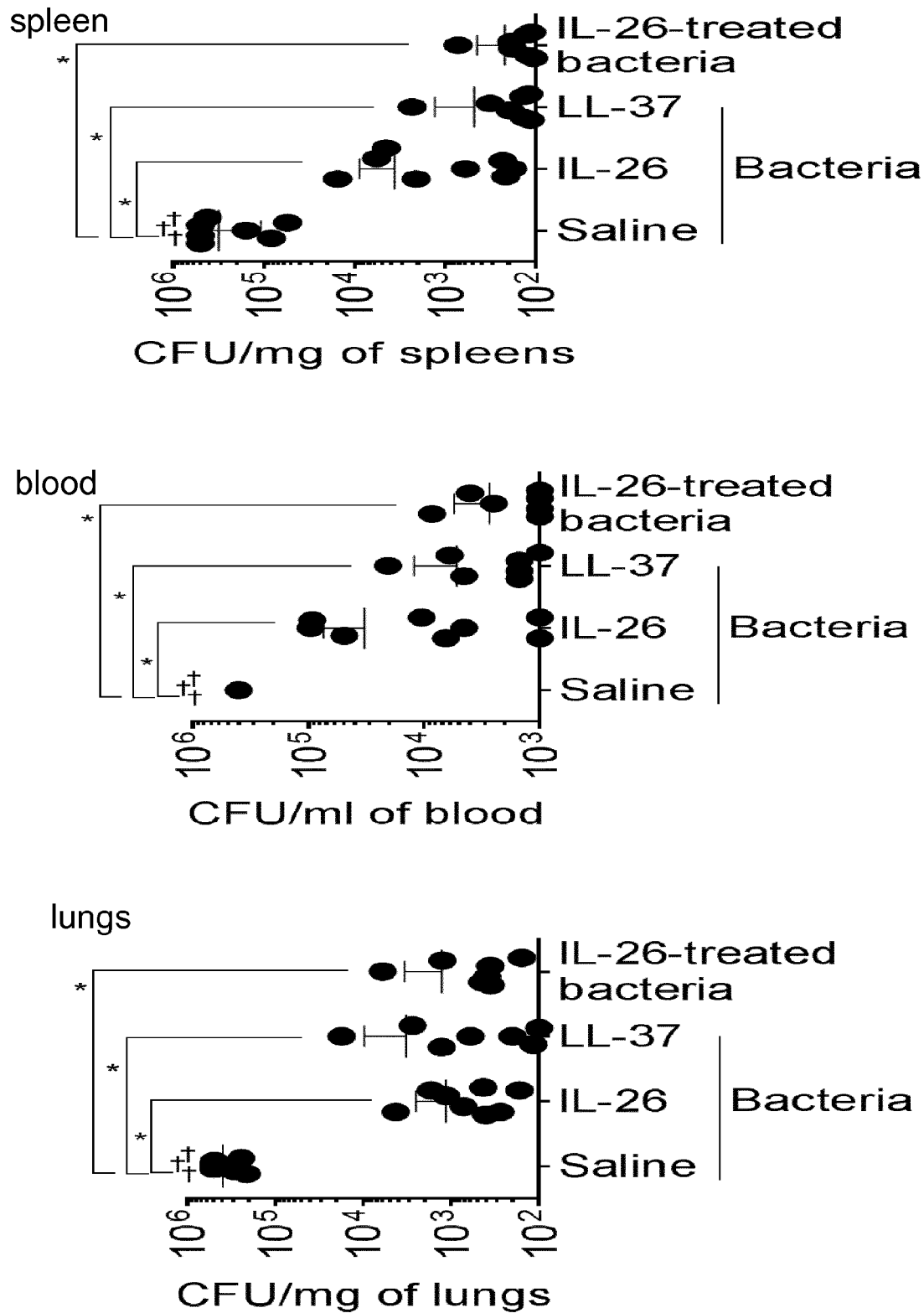
FIG. 1(e), Bacterial loads measured in the lungs, spleen, and blood of mice collected 3 days after i.n. infection with *K. Pneumo* (100 CFU) followed by i.n. treatment with 20 μg rhIL-26, or 50 μg LL-37. As a control, *K. Pneumo* was pretreated ex-vivo with rhIL-26. Each data point represents a separate mouse, † indicated mice that died from overwhelming infection within the 3 days. Data are representative of 4 independent experiments, and were obtained with 8 mice per group. Data were statistically analyzed using unpaired non-parametric Mann-Whitney U test. *$P<0.001$.

The antimicrobial activity of rhIL-26 was tested in vivo using a mouse model *K. pneumonia* sepsis. This model is based on the intranasal administration of *K. pneumonia* (O1:K2) resulting in lung infection followed by a rapid spreading of the bacteria into the circulation and the spleen. Treatment of the mice with IL-26 resulted in significantly reduced bacterial titers in lungs, spleen and blood compared to control mice (FIG. 1e). The in vivo antibacterial activity of IL-26 was comparable to that observed with the antimicrobial peptide LL-37. A strong reduction of the bacterial titers was also observed when bacteria were pretreated in-vitro with IL-26, before intranasal administration. Thus, IL-26 is an antimicrobial protein that efficiently kills extracellular bacteria in vitro and in vivo.

Example 7: TH17 Cells have Antimicrobial Activity Via the Production of IL-26

Figure 2A:
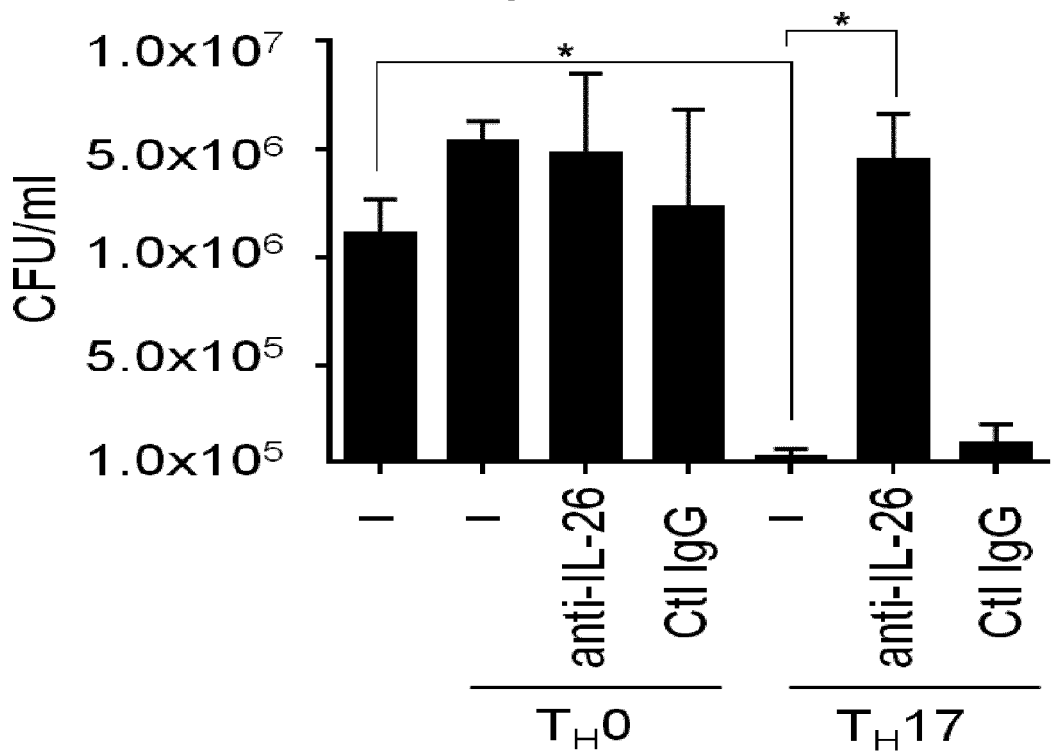
FIG. 2(a), TH17 cells exert direct antimicrobial activity via production of IL-26. Growth of *P. aerug.* cultured with supernatants of primary TH0 and TH17 cells and measured by microbroth dilution assay. Assays were performed with or without blocking anti-IL-26 antibodies or control antibodies (Ctl IgG). Data are representative of 2 independent experiments. Error bars represent the standard deviation of duplicate wells. Data were statistically analyzed using unpaired two-tailed Student's t-test *P<0.05, **P<0.01.
Figure 2B:
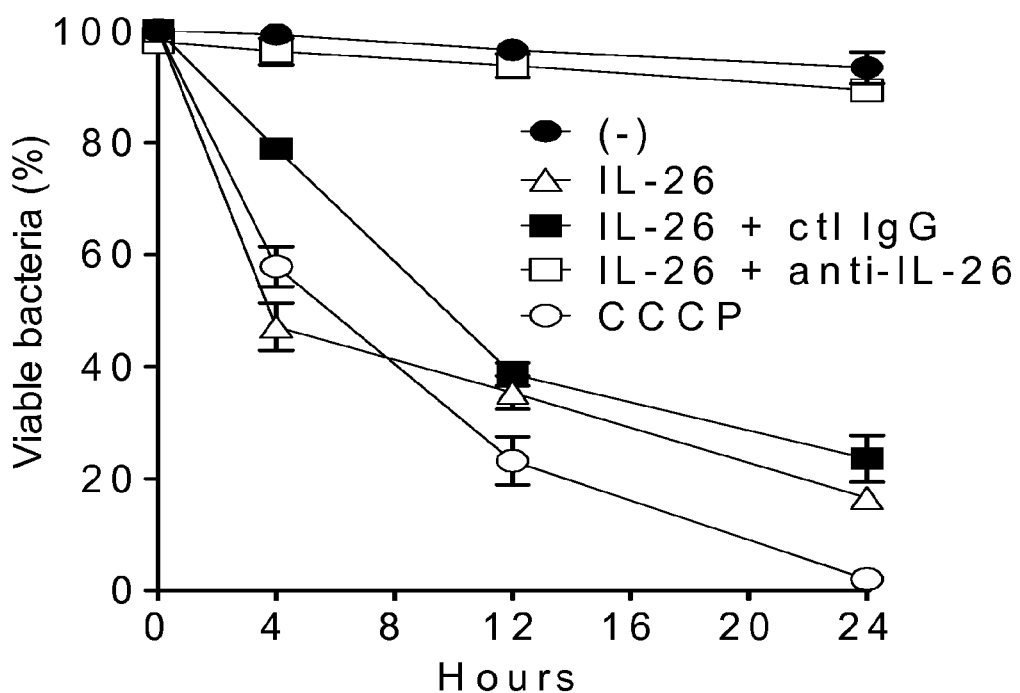
FIG. 2(b), Kinetics of membrane potential of P. aerug. cultured as in (d). Data are representative of 3 independent experiments, error bars represent the standard deviation of duplicate wells.

The ability of the TH17 cells supernatants to kill extracellular bacteria was tested in a microbroth dilution assay. TH17 supernatants but not TH0 supernatants efficiently killed *P. aeruginosa* (FIG. 2a). Bacterial growth was completely restored by addition of the blocking anti-IL-26 antibody (clone 84), which was shown to inhibit killing of bacteria by recombinant IL-26 (FIG. 2b).

Collectively these data reveal a direct antimicrobial capacity of TH17 cells via their production of IL-26.

Example 8: IL-26 Promotes Sensing of DNA Released During Bacterial Killing

Confocal microscopy analysis of *P. aeruginosa* treated with rhIL-26 revealed that dying bacteria released DNA structures that form complexes with IL-26. The ability of IL-26 to bind bacterial DNA was confirmed by mixing fragments of bacterial DNA with increasing concentrations of the IL-26. IL-26 but not IL-17 nor IL-22 efficiently bound to DNA as it decreased the stainability of the DNA and retarded DNA migration in an agarose gel assay. Furthermore, bacterial DNA mixed with IL-26 but not DNA mixed with IL-17 or IL-22 formed insoluble particles showing its ability to package and condense the DNA.

Figure 3A:
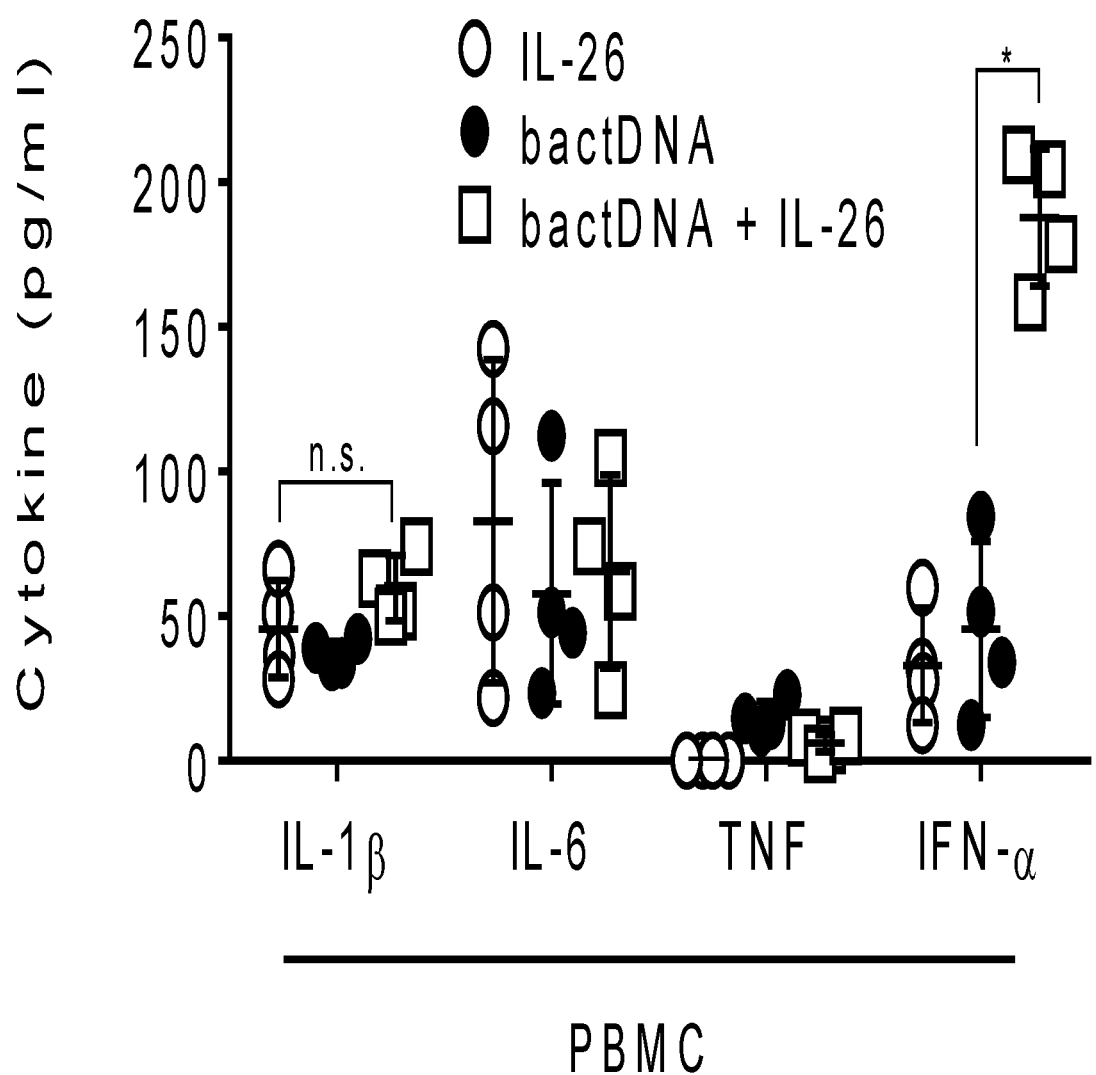
FIG. 3(a), IL-1β, IL-6, TNF, and IFN-α production by PBMC stimulated overnight with 1 μM IL-26 alone or in complex with bacterial DNA (bactDNA, 3 μg/ml). Each data point represents a separate donor (n=4).

The ability of the IL-26-DNA complexes to trigger the production of inflammatory cytokines by human peripheral blood mononuclear cells (PBMC) was tested. IL-26-DNA complexes induced production of IL-1β, IL-6, and IFN-α by PBMC, but only the production of IFN-α was significantly enhanced compared to stimulation with bacterial DNA alone or IL-26 alone (FIG. 3a).

Figure 3B:
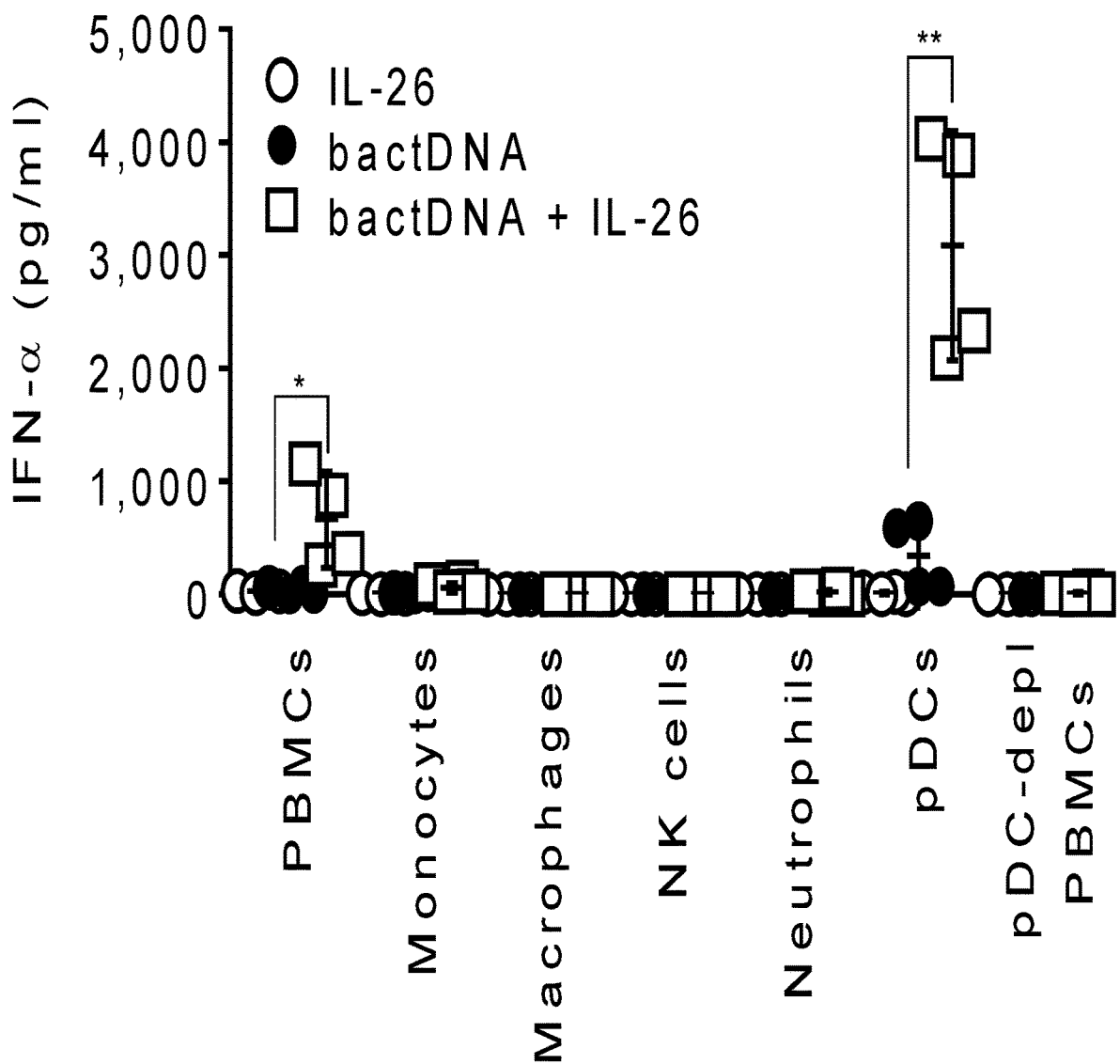
FIG. 3(b), IFN-α produced by human PBMC, monocytes, macrophages, NK cells, neutrophils, pDC and pDC-depleted PBMC stimulated overnight with 1 μM IL-26 alone or in complex with bactDNA. Data points represent 4 independent donors. Mean+SD of the pooled data is shown. Data were statistically analyzed using unpaired two-tailed Student's t-test *P<0.05, **P<0.01. IFN-α produced by pDC stimulated overnight with increasing concentrations (FIG. 3c) of live P. aerug. (P.a.) (titrated according to CFU), or (FIG. 3d) increasing concentration of P. a. lysate (titrated according to DNA content) in the presence or not of IL-26 (10 or 1 μM, respectively).

To determine which cell type was responsible for the production of IFN-α, monocytes, NK cells, neutrophils, plasmacytoid dendritic cells (pDC) and macrophages were stimulated with IL-26-DNA complexes. Only pDC produced high amounts of IFN-α upon stimulation with complexes (FIG. 3b) and depletion of pDC from PBMC completely abrogated their ability to produce IFN-α, indicating that pDC are a key target of bacterial DNA-IL-26 complexes. Purified bacterial DNA alone induced weak or no IFN-α production by pDC (FIG. 3b), whereas IL-26 was unable to induce any IFN-α production in pDC in the absence of DNA. These data demonstrate that IL-26 can form complexes with bacterial DNA and thereby promote the immunogenicity of the DNA leading to IFN-α production by pDC.

Figure 3C:
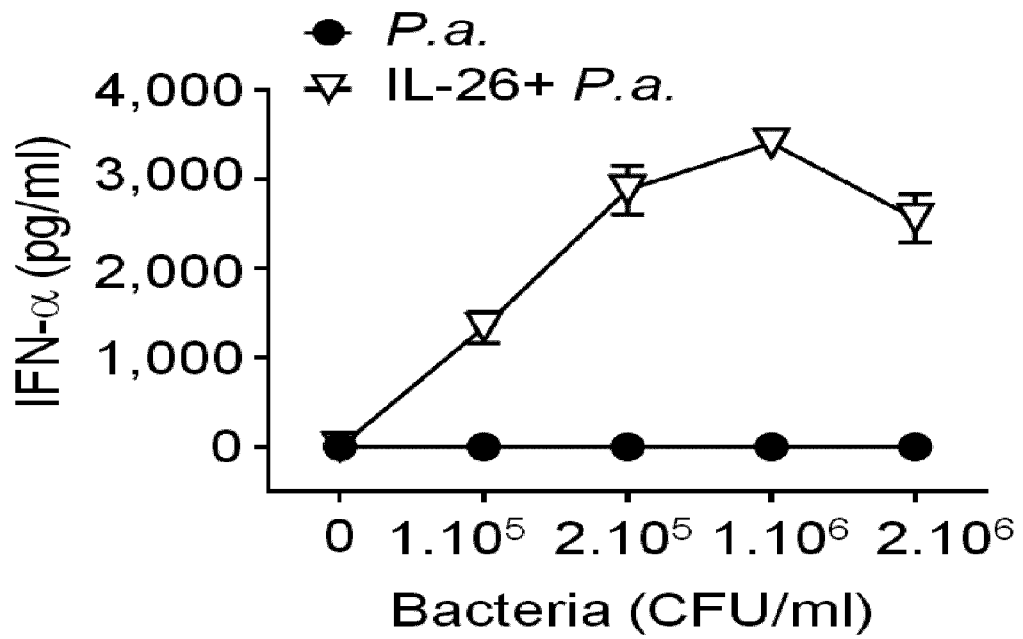
(FIG. 3e) IFN-α produced by pDC stimulated overnight with P.a. lysate (1 μg/ml DNA) or purified bactDNA (1 μg/ml) alone or in the presence of IL-26, with or without DNase pretreatment. (c-e), Error bars represent the standard deviation of triplicate wells. Data are representative of 4 independent experiments. Data were statistically analyzed using unpaired two-tailed Student's t-test *P<0.05, **P<0.01.
Figure 3D:
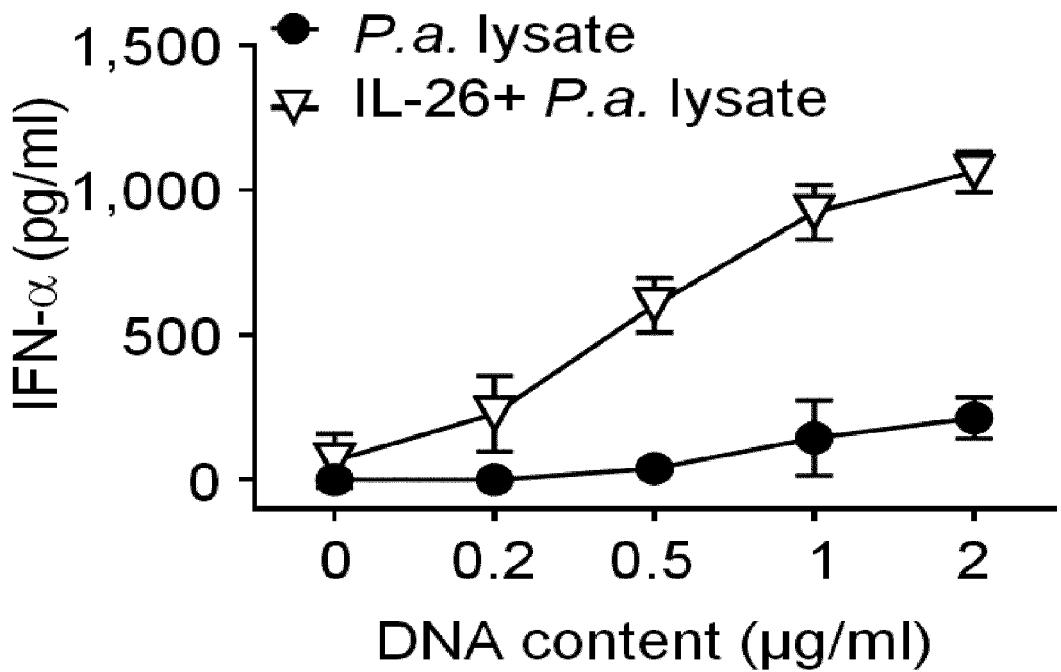

The ability of IL-26-DNA complexes generated in the context of bacterial killing to promote pDC activation was tested. Whereas live *P. aeruginosa* was unable to activate pDC, *P. aeruginosa* killed by IL-26 induced strong IFN-α production (FIG. 3c). Supernatant of *P. aeruginosa* killed by freeze-thaw cycles was also unable to activate pDC, but acquired this ability when mixed with IL-26 (FIG. 3d). In these cultures, IFN-α production paralleled the DNA content and was completely abrogated if DNA was depleted by DNase treatment (FIG. 3e). These indicate that IL-26 has the ability to kill bacteria, bind bacterial DNA and promote its immunogenicity by triggering pDC activation.

Example 9: IL-26 Promotes Sensing of Human DNA Released by Dying Cells

Figure 4A:
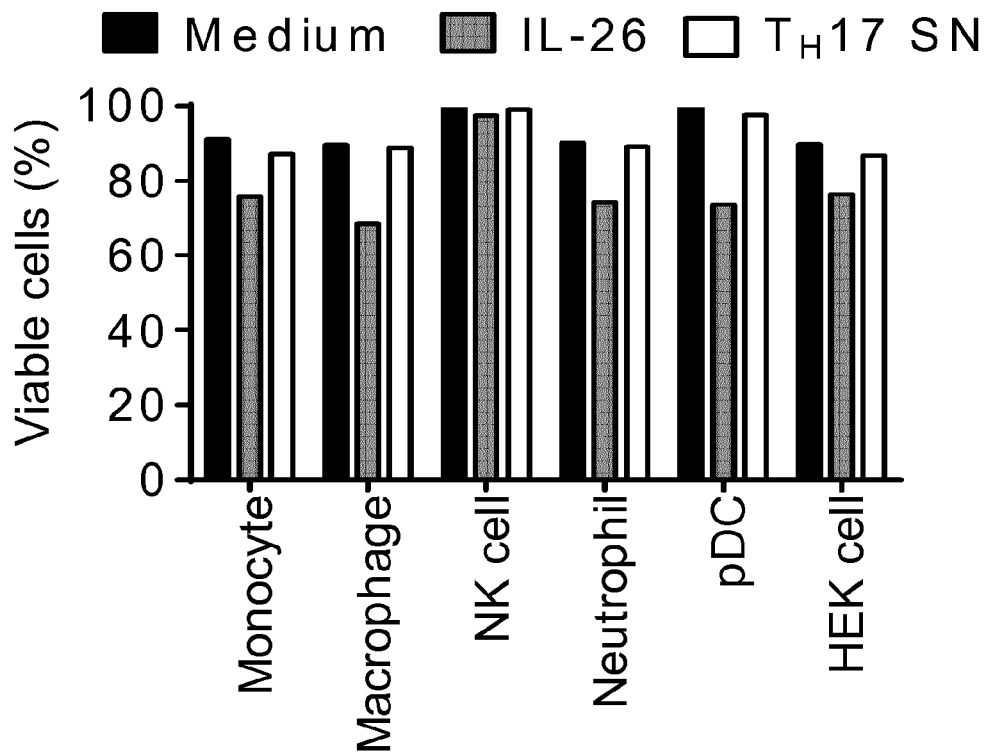
FIG. 4(a). IL-26 promotes pDC sensing of human DNA released in the context of cell death. Cell viability of monocytes, macrophages, NK cells, neutrophils, pDC and HEK cells stained determined by staining with 7-AAD after overnight culture in medium alone or in the presence of either 10 μM of rhIL-26 or undiluted supernatants of primary TH17 cells.
Figure 4B:
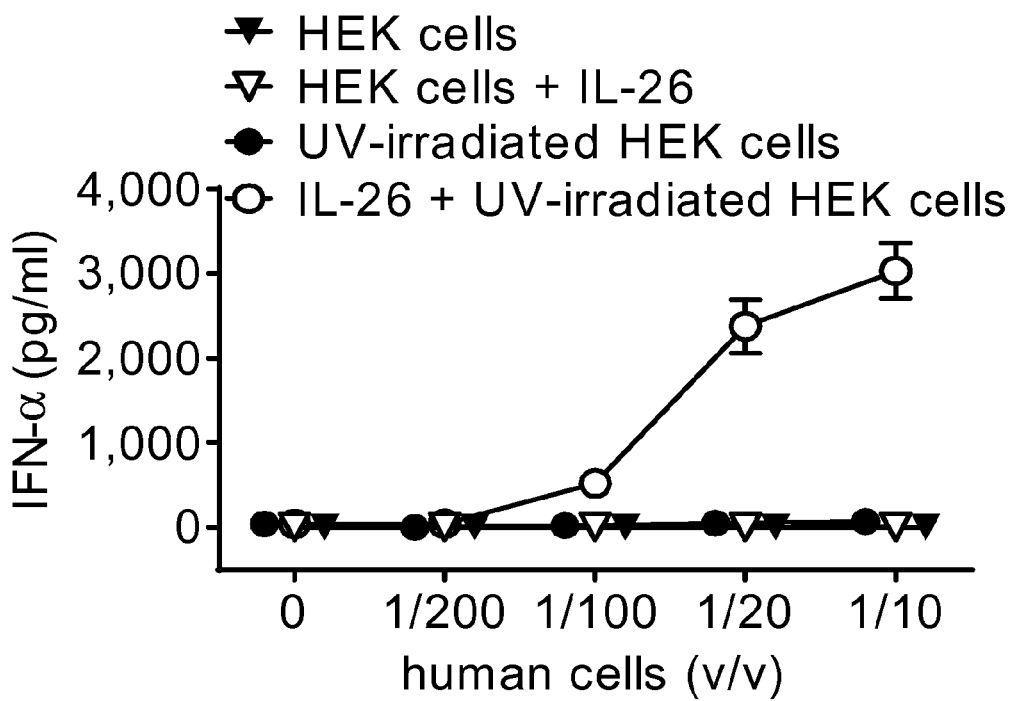
FIG. 4 (b), IFN-α produced by pDC stimulated overnight with live or UV-irradiated HEK 293T cells in the presence or not of 10 μM rhIL-26.
FIG. 4(c), IFN-α produced by human PBMC, monocytes, macrophages, NK cells, neutrophils, pDC and pDC-depleted PBMC stimulated overnight with IL-26 alone, huDNA alone or with IL-26-huDNA complexes. Each data point represents a separate donor (n=4). Mean+SD of the pooled data is shown. Data were statistically analyzed using unpaired two-tailed Student's t-test *P<0.05, **P<0.0001.

The ability of rhIL-26 to kill a range of human cells including HEK cells and primary immune cells was tested. There was no cytotoxic activity at 10 µM, the concentration required for efficient microbial killing (FIG. 4a). Similarly, rhIL-26 mixed with these live human cells did not induce pDC activation (FIG. 4b). However, when rhIL-26 was mixed with irradiated human cells to trigger apoptosis and secondary necrosis, pDC activation was observed (FIG. 4b).

Figure 4C:
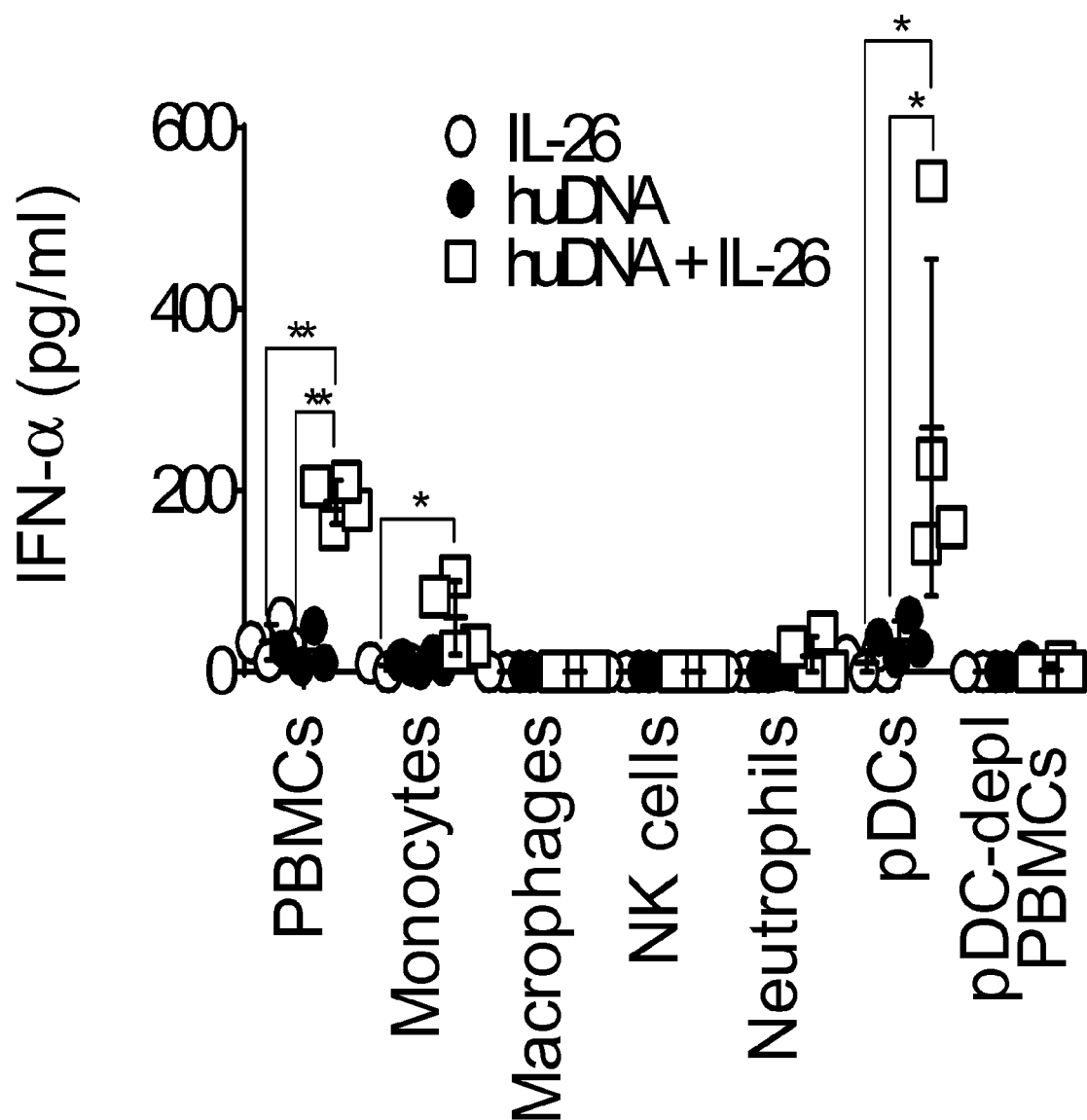
Figure 4D:
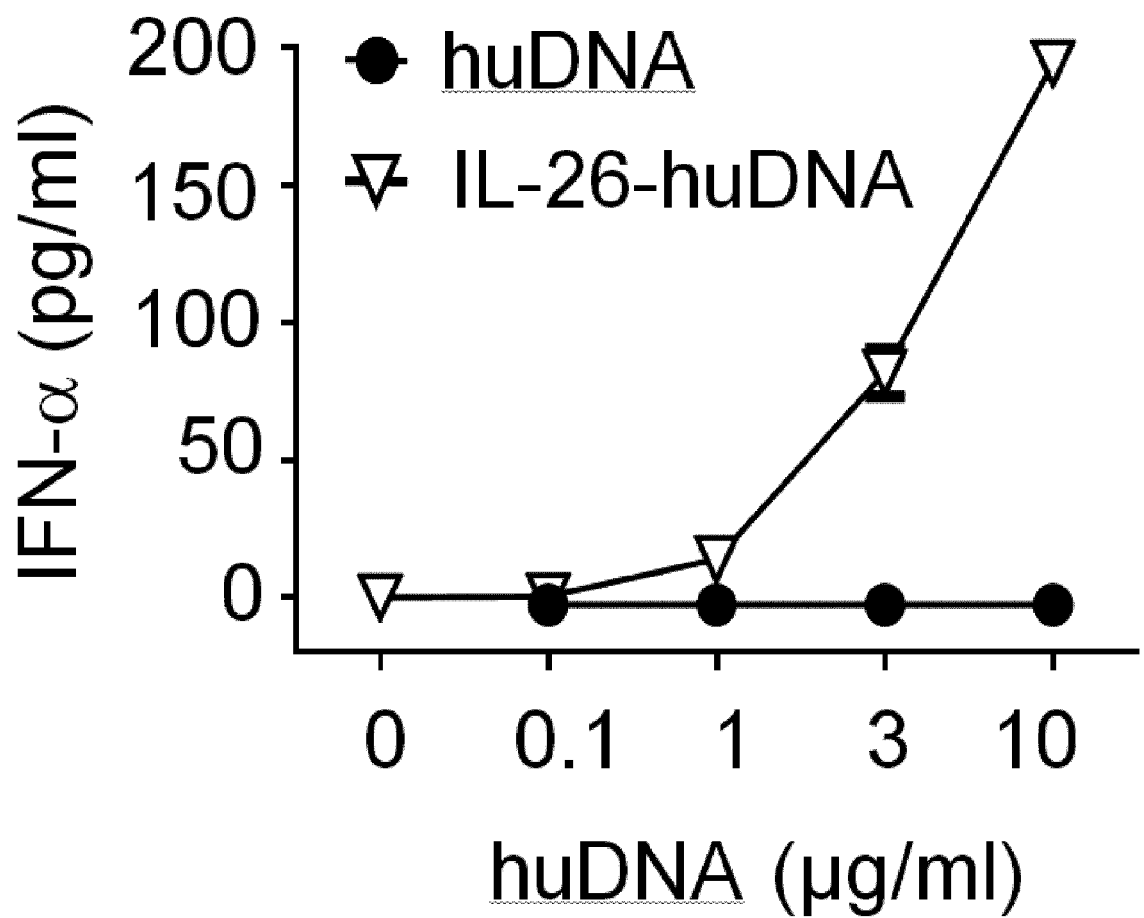

Importantly, human DNA induced IFN-α production in a dose-dependent manner and only in the presence of IL-26 (FIGS. 4c and 4d) confirming that IL-26 converts otherwise non-stimulatory human DNA into a potent activator of pDC. IL-26-human DNA complexes were also found to induce some activation of monocytes to produce small amounts of IFN-α (FIG. 4c), suggesting a broader implication of IL-26 in DNA-mediated innate immune activation, potentially via cytosolic DNA sensors because monocytes do not express TLR9. Furthermore, IL-26 alone was found to trigger activation of purified monocytes to produce some IL-6 and IL-1β, although this activity was intrinsic to IL-26 and not enhanced by the presence of DNA. Taken together these data indicate that effective bacterial concentrations of IL-26 are unable to kill human cells but they do bind human DNA released in the context of cell death leading to pDC activation.

Example 10: IL-26-DNA Complexes are Endocytosed by pDCs and Activate TLR9

Figure 5:
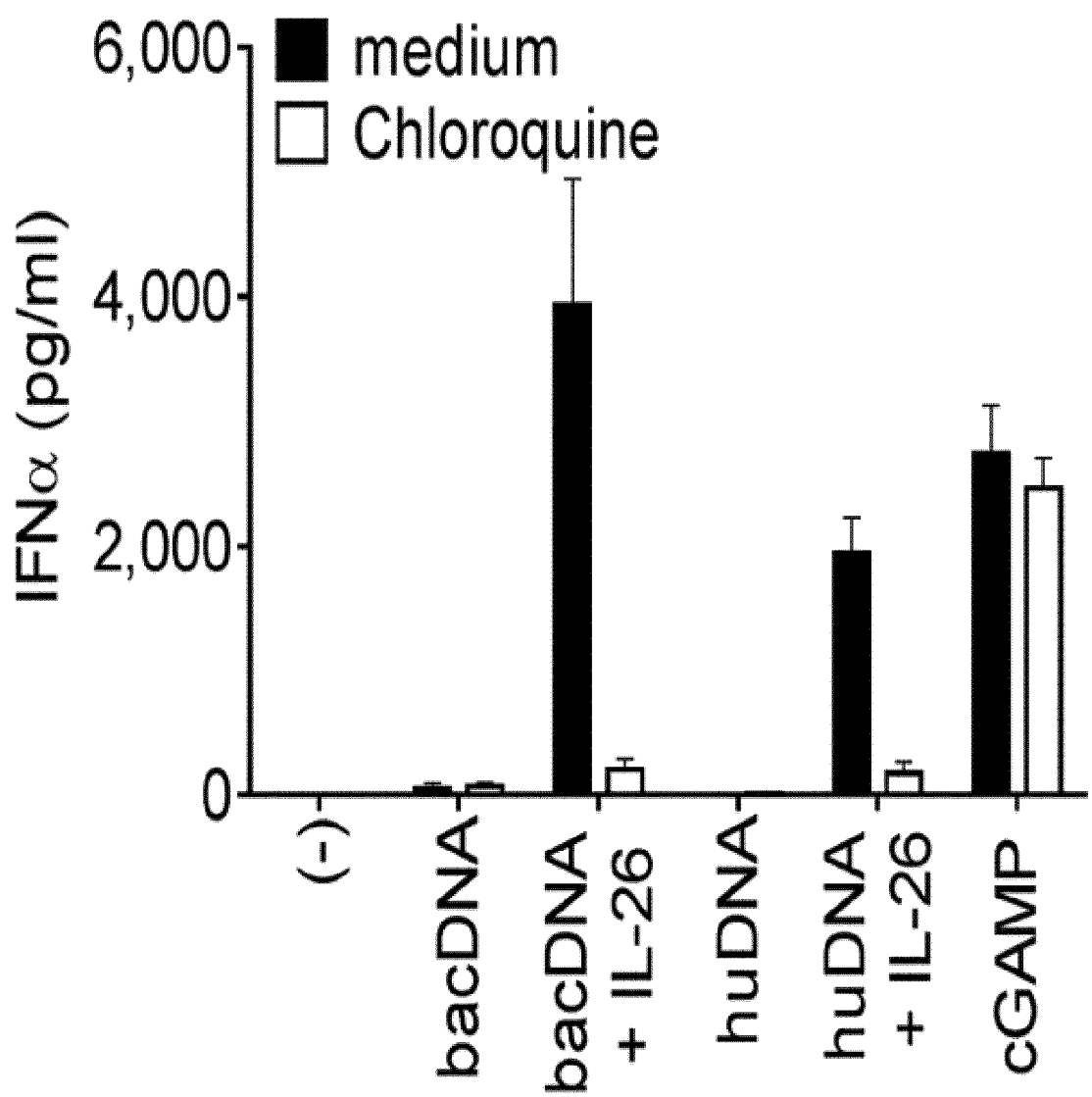
FIG. 5. IL-26-DNA complexes activate endosomal TLR9 in pDCs. IFN-α produced by pDC stimulated overnight with bactDNA or huDNA alone, or with IL-26-bactDNA or IL-26-huDNA complexes, or with the STING ligand cGAMP in the presence of 100 ng/ml chloroquine. Data are representative of 3 independent experiments. Error bars represent the standard deviation of triplicate wells.

Human pDC specifically express TLR9, an endosomal receptor for DNA. To determine whether, upon endosomal entry, IL-26-DNA complexes triggered activation of TLR9, IFN-α production by pDCs pretreated with chloroquine, an inhibitor of endosomal TLR signaling was measured. IFN-α production was completely inhibited by chloroquine (FIG. 5), suggesting the involvement of an endosomal TLR. Importantly, IFN-α production was not inhibited when pDC were treated with chloroquine and activated by cGAMP, which triggers the cytoplasmic sensor STING.

Furthermore IFN-α production was not inhibited by a neutralizing anti-IL-10R2 antibody that blocks activation of the IL-26 receptor or a STAT3 inhibitor that blocks IL-26 receptor signaling. Gain of function experiments using TLR9- and TLR4-transfected HEK293 cells confirmed that IL-26-DNA complexes induced NF-κB activation in TLR9-transfected HEK293 cells but not in TLR4-transfected cells. Thus, IL-26-DNA complexes are endocytosed by pDCs upon attachment to membrane heparan-sulfate proteoglycans and trigger IFN-α production via activation of TLR9.

Example 11: TH17 Cells Promote Innate Activation of pDC by Producing IL-26

Figure 6A:
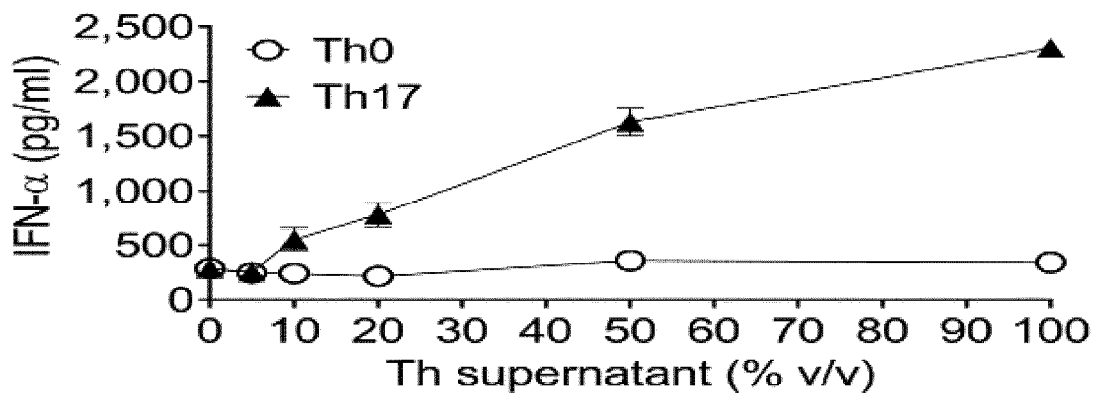
FIG. 6(a). TH17 cells activate pDC via IL-26 production. IFN-α produced by pDC stimulated overnight with various dilutions of TH17 cell-derived supernatants in culture medium (v/v).
Figure 6B:
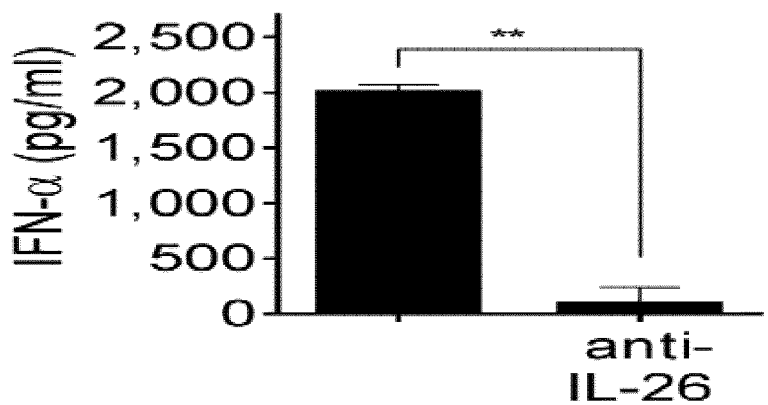
FIG. 6(b). IFN-α produced by pDC stimulated overnight with supernatant derived from TH17 cells restimulated in the presence of neutralizing anti-IL-26 antibodies. Error bars represent the standard deviation of triplicate wells. Data are representative of 3 independent experiments. Statistical analysis was done using unpaired two-tailed Student's t-test; **P<0.001.
Figure 6C:
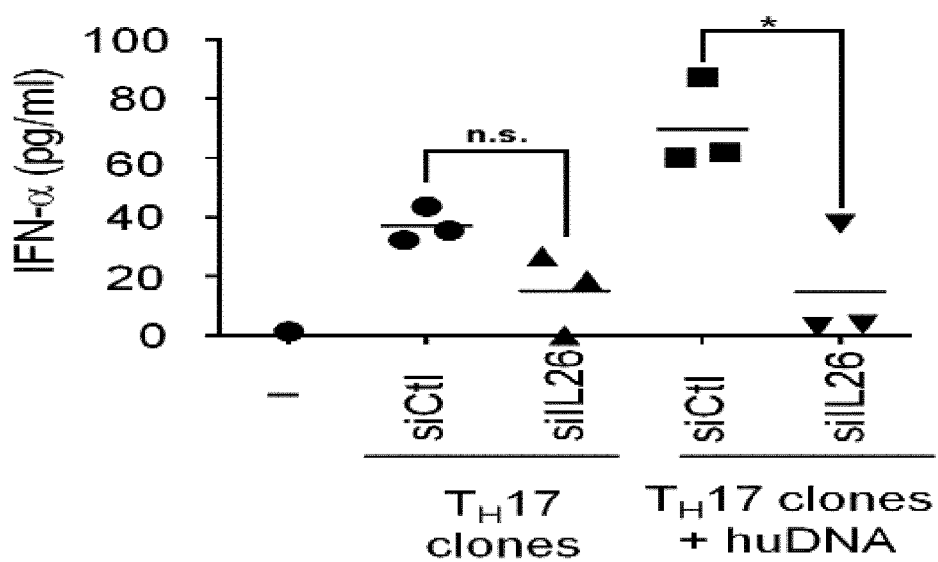
FIG. 6(c), IFN-α produced by pDC stimulated overnight with supernatants of TH17 clones (n=3) transfected with siRNA against IL-26 (siIL26) or a control siRNA (siCtl) supplemented or not by huDNA. Data are representative of at least 3 independent experiments. Data were statistically analyzed using unpaired two-tailed Student's t-test *P<0.05.

The production of high amounts of IL-26 by TH17 cells is shown on FIG. 6a. Particles were numerous in TH17 supernatants compared to supernatants of other TH cells including TH0 cells. To determine whether these natural IL-26-DNA complexes present in TH17 supernatants trigger IFN-α by pDC, purified pDC were stimulated with the TH17 supernatants. TH17 supernatants induced IFN-α production by pDC (FIG. 6a), which was inhibited by addition of an anti-IL-26 antibody that blocks binding to DNA and inhibits pDC activation (FIG. 6b) or by DNase pretreatment of the supernatants. Supernatants of TH17 clones expressing IL-26 were also able to induce IFN-α production by pDC, which was inhibited by siRNA-mediated knock-down of IL-26 (FIG. 6c). Addition of exogenous DNA to the cultures enhanced IFN production by pDC and confirmed that activation was driven by IL-26 as knockdown experiments completely blocked IFN production by pDC (FIG. 6c).

Figure 6D:
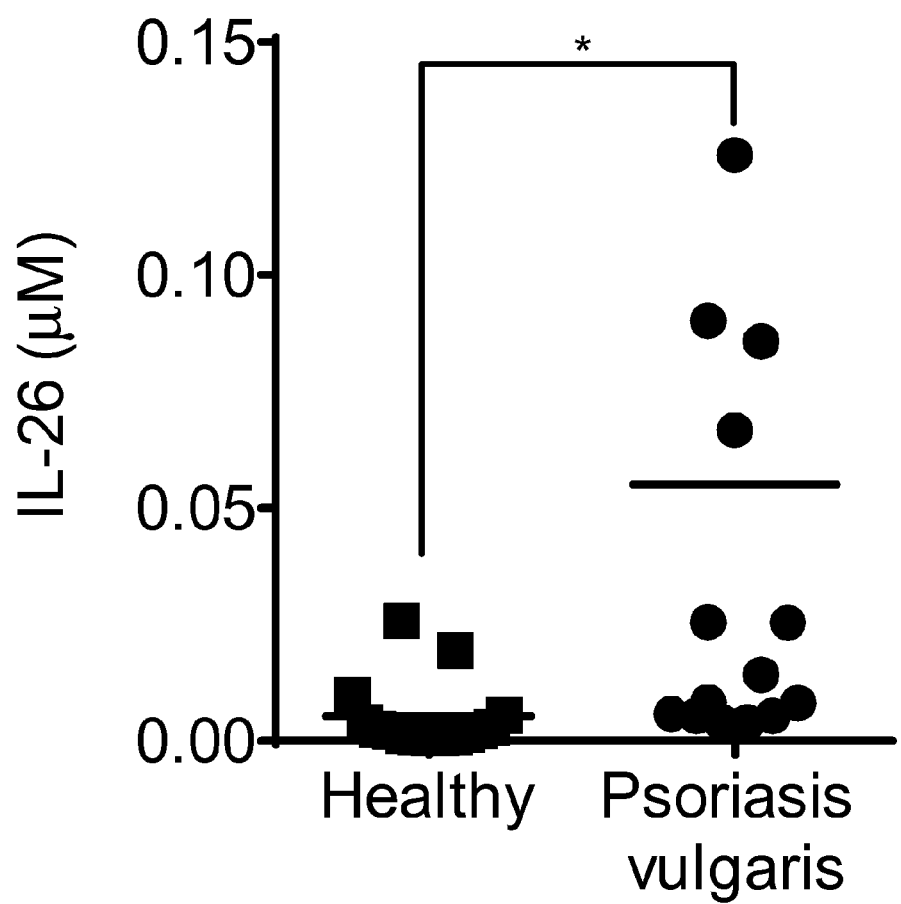
FIG. 6(d), IL-26 concentrations in healthy skin and psoriatic skin lesions measured by ELISA of total skin extracts derived from healthy donors (n=15) or psoriasis patients (n=15). Each data point represents a separate donor. Data were statistically analyzed using unpaired non parametric Mann-Whitney U test *P<0.001.

These findings suggest that TH17-derived IL-26 drives innate immune activation of pDC through the formation of complexes with human DNA released into the extracellular environment during cell turnover. There was no difference between the concentration of natural IL-26 contained in TH17-supernatants and the concentration of rhIL-26 required to induce IFN-α production in pDC. Both recombinant and natural IL-26 induced IFN-α production by pDC at 0.1 μM, a concentration which appeared to be relevant in vivo, as tissue concentrations up to 0.15 μM were measured in patient psoriatic skin lesions known to contain large numbers of activated pDCs producing IFN-α (FIG. 6d).

The invention claimed is:

1. An isolated monoclonal antibody or biological active fragment thereof that binds to inhibit IL-26, comprising: a heavy chain variable region that comprises CDR1, CDR2, CDR3 sequences and a light chain variable region that comprises CDR1, CDR2, CDR3 sequences wherein:
 (a) the heavy chain variable region CDR1 sequence consisting of the amino acid sequence of SEQ ID NO: 5;
 (b) the heavy chain variable region CDR2 sequence consisting of the amino acid sequence of SEQ ID NO: 6;
 (c) the heavy chain variable region CDR3 sequence consisting of the amino acid sequence of SEQ ID NO: 7;
 (d) the light chain variable region CDR1 sequence consisting of the amino acid sequence of SEQ ID NO: 8;
 (e) the light chain variable region CDR2 sequence consisting of the amino acid sequence of SEQ ID NO: 9;
 (f) the light chain variable region CDR3 sequence consisting of the amino acid sequence of SEQ ID NO: 10;
 and wherein said isolated monoclonal antibody or biological active fragment thereof specifically inhibits the receptor-independent inflammatory function of IL-26.

2. The isolated monoclonal antibody or a biological active fragment thereof capable of binding and inhibiting IL-26 according to claim 1, wherein said monoclonal antibody or biological active fragment thereof comprises:
 i) a Heavy Chain Variable Region (HCVR) comprising the amino acid sequence of SEQ ID NO: 3, and
 ii) a Light Chain Variable Region (LCVR) comprising the amino acid sequence of SEQ ID NO: 4.

3. The isolated monoclonal antibody or biological active fragment thereof capable of binding and inhibiting IL-26 according to claim 2, consisting of:
 a heavy chain comprising the amino acid sequence of SEQ ID NO: 3 and a light chain comprising the amino acid sequence of SEQ ID NO: 4.

4. A pharmaceutical composition comprising the isolated monoclonal antibody or the biological active fragment thereof according to claim 1, and optionally further comprising a pharmaceutically acceptable carrier.

5. The pharmaceutical composition of claim 4, further comprising one or more of the following: a biologically active substance, a diluent, or an excipient.

6. The pharmaceutical composition according to claim 5, further comprising a biologically active substance which is a compound used in the treatment of inflammatory diseases.

7. The pharmaceutical composition of claim 4, wherein the compound is selected from the group consisting of methotrexate, cyclosporin, fumaric acid, Neotigason; TNF blockers selected among elanarcept, adalimumab, infliximab; IL-12/23p40 blockers; anti-IL-17 antibodies selected among secukinumab, ixekinumab; Apremilast, tofacitinib.

8. A method for the treatment or alleviation of the effects of inflammatory diseases wherein the method comprises the administration to a patient in need thereof of the isolated monoclonal antibody or the biological active fragment thereof according to claim 1.

9. The method of claim 8, wherein the inflammatory diseases are selected among the group comprising psoriasis, Crohn's disease, rheumatoid arthritis, ankylosing spondylitis, multiple sclerosis.

10. The method according to claim 8, wherein the treatment of the effects of inflammatory diseases in a patient, leads to a decrease in the:
 a—Lesional type I IFN production (IFN-α or IFN-β) and decrease of type I IFN induced gene expression;
 b—cell infiltration and the expression of the inflammatory genes IL-6, TNF, IL-12, IL-23, IL-8, IL-17, IL-22, IFN-γ.

11. The method according to claim 8, wherein the treatment of psoriasis in a patient, further leads to a decrease in the:
 i—epidermal thickening on histology (acanthosis and papillomatosis) and the clinical resolution of the plaque
 ii—the PASI score.

12. An isolated monoclonal antibody that binds and inhibits IL-26, wherein said isolated monoclonal antibody has the same epitope specificity as a monoclonal antibody produced by hybridoma cell line 142-84-B1, ATCC accession number PTA-122358, and wherein said isolated monoclonal antibody comprises:
 a heavy chain variable region that comprises CDR1, CDR2, CDR3 sequences and a light chain variable region that comprises CDR1, CDR2, CDR3 sequences wherein:
 (a) the heavy chain variable region CDR1 sequence comprising the amino acid sequence of SEQ ID NO: 5;

(b) the heavy chain variable region CDR2 sequence comprising the amino acid sequence of SEQ ID NO: 6;
(c) the heavy chain variable region CDR3 sequence comprising the amino acid sequence of SEQ ID NO: 7;
(d) the light chain variable region CDR1 sequence comprising the amino acid sequence of SEQ ID NO: 8;
(e) the light chain variable region CDR2 sequence comprising the amino acid sequence of SEQ ID NO: 9;
(f) the light chain variable region CDR3 sequence comprising the amino acid sequence of SEQ ID NO: 10, or said isolated monoclonal antibody comprises:

i) a Heavy Chain Variable Region (HCVR) comprising the amino acid sequence of SEQ ID NO: 3, and ii) a Light Chain Variable Region (LCVR) comprising the amino acid sequence of SEQ ID NO: 4.

13. The isolated monoclonal antibody according to claim 12, wherein said isolated monoclonal antibody is produced by hybridoma cell line 142-84-B1, ATCC accession number PTA-122358.

\* \* \* \* \*

SEQUENCE LISTING

```
<160> NUMBER OF SEQ ID NOS: 10

<210> SEQ ID NO 1
<211> LENGTH: 348
<212> TYPE: DNA
<213> ORGANISM: Mus musculus

<400> SEQUENCE: 1
caggttcaac tgcagcagtc tggggctgag ctggtgaggc ctggggcttc agtgacgctg      60
tcctgcaagg cctcgggctt cacatttcct gactatgaaa tacactgggt gaggcagaca     120
cctgtgcatg gcctggaatg gattggaggt attgatcctg aaactggtga tactgccaac     180
aatcagaagt tcaagggcaa ggccacactg actgcagaca catcctccag cacagcctac     240
atggagctcc gcagcctgac atctgaggac tcagccgtct attactgtac aagattctac     300
ggtagttttg actactggga ccaaggcacc actctcacag tctcctca                  348

<210> SEQ ID NO 2
<211> LENGTH: 336
<212> TYPE: DNA
<213> ORGANISM: Mus musculus

<400> SEQUENCE: 2
aacattatga tgacacagtc gccatcatct ctggctgtgt ctgcaggaga aaaggtcact      60
ctgagctgta agtccagtca aagtgtttta tacagttcaa atcagaaaaa ttacttggcc     120
tggtaccagc agaaaccagg gcagtctcct aaactactga tctactgggc atccactagg     180
gaatctggtg tccctgatcg cttcacaggc agtggatctg ggacagattt tactcttacc     240
atcagcagtg tacaagctga agacctggca gtttattact gtcatcaata cctctcctcg     300
tacacgttcg gagggggggac caagctggaa ataaaa                              336

<210> SEQ ID NO 3
<211> LENGTH: 116
<212> TYPE: PRT
<213> ORGANISM: Mus musculus

<400> SEQUENCE: 3

Gln Val Gln Leu Gln Gln Ser Gly Ala Glu Leu Val Arg Pro Gly Ala
1               5                   10                  15

Ser Val Thr Leu Ser Cys Lys Ala Ser Gly Phe Thr Phe Pro Asp Tyr
            20                  25                  30

Glu Ile His Trp Val Arg Gln Thr Pro Val His Gly Leu Glu Trp Ile
        35                  40                  45

Gly Gly Ile Asp Pro Glu Thr Gly Asp Thr Ala Asn Asn Gln Lys Phe
    50                  55                  60

Lys Gly Lys Ala Thr Leu Thr Ala Asp Thr Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Phe Tyr Gly Ser Phe Asp Tyr Trp Asp Gln Gly Thr Thr Leu
            100                 105                 110
```

```
Thr Val Ser Ser
        115

<210> SEQ ID NO 4
<211> LENGTH: 112
<212> TYPE: PRT
<213> ORGANISM: Mus musculus

<400> SEQUENCE: 4

Asn Ile Met Met Thr Gln Ser Pro Ser Ser Leu Ala Val Ser Ala Gly
1               5                   10                  15

Glu Lys Val Thr Leu Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Leu Ser Ser Tyr Thr Phe Gly Gly Gly Thr Lys Leu Glu Ile Lys
            100                 105                 110

<210> SEQ ID NO 5
<211> LENGTH: 10
<212> TYPE: PRT
<213> ORGANISM: Mus musculus

<400> SEQUENCE: 5

Gly Phe Thr Phe Pro Asp Tyr Glu Ile His
1               5                   10

<210> SEQ ID NO 6
<211> LENGTH: 17
<212> TYPE: PRT
<213> ORGANISM: Mus musculus

<400> SEQUENCE: 6

Gly Ile Asp Pro Glu Thr Gly Asp Thr Ala Asn Asn Gln Lys Phe Lys
1               5                   10                  15

Gly

<210> SEQ ID NO 7
<211> LENGTH: 7
<212> TYPE: PRT
<213> ORGANISM: Mus musculus

<400> SEQUENCE: 7

Phe Tyr Gly Ser Phe Asp Tyr
1               5

<210> SEQ ID NO 8
<211> LENGTH: 17
<212> TYPE: PRT
<213> ORGANISM: Mus musculus

<400> SEQUENCE: 8

Lys Ser Ser Gln Ser Val Leu Tyr Ser Ser Asn Gln Lys Asn Tyr Leu
1               5                   10                  15

Ala
```

```
<210> SEQ ID NO 9
<211> LENGTH: 7
<212> TYPE: PRT
<213> ORGANISM: Mus musculus

<400> SEQUENCE: 9

Trp Ala Ser Thr Arg Glu Ser
1               5

<210> SEQ ID NO 10
<211> LENGTH: 8
<212> TYPE: PRT
<213> ORGANISM: Mus musculus

<400> SEQUENCE: 10

His Gln Tyr Leu Ser Ser Tyr Thr
1               5
```